(12) United States Patent
Gellman et al.

(10) Patent No.: US 6,679,896 B2
(45) Date of Patent: Jan. 20, 2004

(54) TRANSVAGINAL SUTURE SPACER DEVICES AND METHODS OF USE

(75) Inventors: Barry N. Gellman, North Easton, MA (US); Ghaleb A. Sater, Lynnfield, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/109,021

(22) Filed: Mar. 28, 2002

(65) Prior Publication Data

US 2002/0099391 A1 Jul. 25, 2002

Related U.S. Application Data

(62) Division of application No. 09/184,468, filed on Nov. 2, 1998.

(51) Int. Cl.[7] .................................................. A61B 17/04
(52) U.S. Cl. ........................................ 606/148; 606/139
(58) Field of Search ............................ 606/148, 139, 606/228, 232, 144; 600/29, 30; 289/1.5

(56) References Cited

U.S. PATENT DOCUMENTS

| | | | |
|---|---|---|---|
| 246,648 A | 9/1881 | Wilcox | |
| 620,853 A | 7/1899 | Richter | 606/208 |
| 724,034 A | 3/1903 | Nuttall | 606/158 |
| 2,199,025 A | 4/1940 | Conn | |
| 3,287,042 A | 11/1966 | Baer | 289/17 |
| 3,476,423 A | 11/1969 | Kentfield | 289/17 |
| 3,580,313 A | 5/1971 | McKnight | 145/46 |
| 3,705,575 A | 12/1972 | Edwards | 128/1 R |
| 3,710,592 A | 1/1973 | Scow | 66/1 A |
| 3,744,495 A | 7/1973 | Johnson | 128/337 |
| RE27,735 E | 8/1973 | Shave et al. | 606/226 |
| 3,782,764 A | 1/1974 | Browning | 289/1.2 |
| 3,857,396 A | 12/1974 | Hardwick | 128/335 |
| 4,085,756 A | 4/1978 | Weaver | 128/303.17 |
| 4,172,458 A | 10/1979 | Pereyra | 128/340 |
| 4,210,148 A | 7/1980 | Stivala | 128/335 |
| 4,400,833 A | 8/1983 | Kurland | 3/1 |
| 4,409,974 A | 10/1983 | Freedland | 128/92 B |
| 4,414,967 A | 11/1983 | Shapiro | 128/92 B |
| 4,545,374 A | 10/1985 | Jacobson | 128/303 R |
| 4,586,503 A | 5/1986 | Kirsch et al. | 606/155 |
| 4,741,330 A | 5/1988 | Hayhurst | 128/92 YF |
| 4,784,126 A | 11/1988 | Hourahane | 128/92 YF |
| D299,168 S | 12/1988 | Bergstrom et al. | D24/27 |

(List continued on next page.)

FOREIGN PATENT DOCUMENTS

| | | |
|---|---|---|
| EP | 0 599 772 A1 | 6/1994 |
| GB | 2214814 A | 9/1989 |
| GB | 2268690 | 1/1994 |

(List continued on next page.)

OTHER PUBLICATIONS

Benderev: A modified Percutaneous outpatient Bladder Neck Suspension system, J. Urology 152: 2316–2320 (1994).

(List continued on next page.)

Primary Examiner—David H. Willse
Assistant Examiner—Brian E Pellegrino
(74) Attorney, Agent, or Firm—Testa, Hurwitz & Thibeault LLP

(57) ABSTRACT

The present invention relates to suture spacers and methods for their use. More particularly, the present invention relates to devices which permit a surgeon to create a consistent amount of suture slack in a suture line when tying sutures under very tight space constraints including procedures such as bladder neck stabilization and treatment of hypermobility or intrinsic sphincter deficiency. Further, the present invention relates to methods of tying sutures using the disclosed devices in such procedures.

8 Claims, 10 Drawing Sheets

U.S. PATENT DOCUMENTS

| | | | |
|---|---|---|---|
| 4,792,330 A | 12/1988 | Lazarus et al. | 606/158 |
| 4,854,316 A | 8/1989 | Davis | 128/334 R |
| 4,857,041 A | 8/1989 | Annis et al. | 600/30 |
| 4,872,451 A | 10/1989 | Moore et al. | 128/92 YF |
| 4,873,977 A | 10/1989 | Avant et al. | 128/334 R |
| 4,938,760 A | 7/1990 | Burton et al. | 600/29 |
| 4,969,892 A | 11/1990 | Burton et al. | 606/218 |
| 5,012,822 A | 5/1991 | Schwarz | 128/885 |
| 5,013,292 A | 5/1991 | Lemay | 600/30 |
| 5,019,032 A | 5/1991 | Robertson | 600/29 |
| 5,064,434 A | 11/1991 | Haber | 623/11 |
| 5,078,731 A | 1/1992 | Hayhurst | 606/232 |
| 5,084,058 A | 1/1992 | Li | 606/148 |
| 5,087,263 A | 2/1992 | Li | 606/148 |
| 5,112,344 A | 5/1992 | Petros | 606/148 |
| 5,149,329 A | 9/1992 | Richardson | 604/272 |
| 5,163,946 A | 11/1992 | Li | 606/148 |
| 5,219,359 A | 6/1993 | McQuilkin et al. | 606/232 |
| 5,256,133 A | 10/1993 | Spitz | 600/29 |
| 5,328,077 A | 7/1994 | Lou | 227/175 |
| 5,405,352 A | 4/1995 | Weston | 606/148 |
| 5,437,603 A | 8/1995 | Cerny et al. | 600/29 |
| 5,445,167 A | 8/1995 | Yoon et al. | 606/139 |
| 5,474,543 A | 12/1995 | McKay | 604/272 |
| 5,527,342 A | 6/1996 | Pietrzak et al. | 606/232 |
| 5,544,664 A | 8/1996 | Benderev et al. | 128/898 |
| 5,591,163 A | 1/1997 | Thompson | 606/29 |
| 5,591,177 A | 1/1997 | Lehrer | 606/139 |
| 5,611,515 A | 3/1997 | Benderev et al. | 128/898 |
| 5,643,288 A | 7/1997 | Thompson | 606/139 |
| 5,649,940 A | 7/1997 | Hart et al. | 606/148 |
| 5,690,655 A | 11/1997 | Hart et al. | 606/148 |
| 5,697,931 A | 12/1997 | Thompson | 606/72 |
| 5,716,368 A | 2/1998 | de la Torre et al. | 606/148 |
| 5,807,403 A | 9/1998 | Beyar et al. | 606/232 |
| 5,816,258 A | 10/1998 | Jervis | 128/898 |
| 5,846,254 A | 12/1998 | Schulze et al. | 606/228 |
| 6,039,686 A | 3/2000 | Kovac | 600/30 |
| 6,042,534 A | 3/2000 | Gellman et al. | 600/30 |
| 6,221,005 B1 | 4/2001 | Bruckner et al. | 600/30 |

FOREIGN PATENT DOCUMENTS

| | | |
|---|---|---|
| JP | 6-114067 | 4/1994 |
| SE | 503 271 | 3/1996 |
| SE | 506 164 | 4/1997 |
| WO | WO 92/16152 | 10/1992 |
| WO | WO 93/10715 | 6/1993 |
| WO | WO 93/19678 | 10/1993 |
| WO | WO 96/06567 | 3/1996 |
| WO | WO 97/13465 | 4/1997 |
| WO | WO 97/30638 | 8/1997 |
| WO | WO 97/43982 | 11/1997 |
| WO | WO 98/12971 | 4/1998 |

OTHER PUBLICATIONS

Forneret: Cost–effective treatment of female stress urinary incontinence: modified pereyra bladder neck suspension, Urology 25: 365–367 (1985).

Gittes: No–incision pubovaginal suspension for stress incontinence, J. Urology 138: 568–570 (1987).

Hancock: Transpubic suspension of the Bladder Neck for Urinary Incontinence, J. Urology 123: 667–668 (1980).

Leach: Modified Pereyra Bladder Neck Suspension after previously failed anti–incontinence surgery: Surgical Technique and Results with long–term follow–up, Urology 23: 359–362 (1984).

Leach: Percutaneous Bladder Neck Suspension, Urol Clinics of N. Am. 23: 511–516 (1996).

Leach: Bone fixation technique for transvaginal needle suspension, Urology 31: 388–390 (1988).

McGuire: The Sling Procedure for Urinary Stress Incontinence, Profiles in Urology—The Sling Procedure for Urinary Stress Incontinence.

McKiel: Marshall–Marchetti Procedure: Modification, J. Urology 96: 737–739 (1966).

Pereyra: A Simplified Surgical Procedure for the Correction of Stress Incontinence in Women, West. J. Surg. Obstetrics and Gynecology: 223–226 (1959).

Raz: Modified Bladder Neck Suspension for Female Stress Incontinence, Urology 17: 82–85 (1981).

Schaeffer: Endoscopic suspension of vesical neck for urinary incontinence, Urology 23: 484–494 (1984).

Schatzker: *The Rationale of Operative Fracture Care*; Springer–Verlag: Berlin, 1987, 159.

Scheuer: The Modified Pereyra Bladder Neck Suspension Procedure: Using Mitek® GII Anchors, Mitek® Brochure (1993).

Spencer: A comparison of Endoscopic suspension of the vesical neck with suprapubic vesicourethropexy for treatment of stress urinary incontinence, J. Urology 137: 411–415 (1987).

Stamey: Endoscopic Suspension of the Vesical Neck for Urinary Incontinence in Females: Report on 203 Consecutive patients, Ann. Surg. 192: 465–471 (1980).

Stamey: "Endoscopic Suspension of the Vesical Neck", *Surgery of Female Incontinence*, 115–132.

Stamey: Endoscopic Suspension of the vesical neck for urinary incontinence, Surgery, Gynecology and Obstetrics 136: 547–554 (1973).

Webster: "Female Urinary Incontinence," *Urologic Surgery*, J.B. Lippincott Company: Philadelphia, 1983, 665–679.

Winter: Peripubic urethropexy for urinary stress incontinence in women, Urology 20: 408–411 (1982).

Zimmern: A prospective evaluation of Four–Corner bladder neck suspension for Grade 11/111 Cystocele repair, Neurol. and Urodynamics 9: 231 (1990).

Zimmern: Transvaginal Closure of the Bladder Neck, Seminars in Urology 4: 30–32 (1986).

Araki et al., "The Loop–Loosening Procedure for Urination Difficulties After Stamey Suspension of the Vesical Neck," *The Journal of Urology*, 144:319–323.

Benderev, "Anchor Fixation and Other Modifications of Endoscopic Bladder Neck Suspension," *Urology*, 40(5):409–418 (1992).

Blaivas, "Successful Pubovaginal Sling Surgery," *Contemporary Urology*, 40–63 (1993).

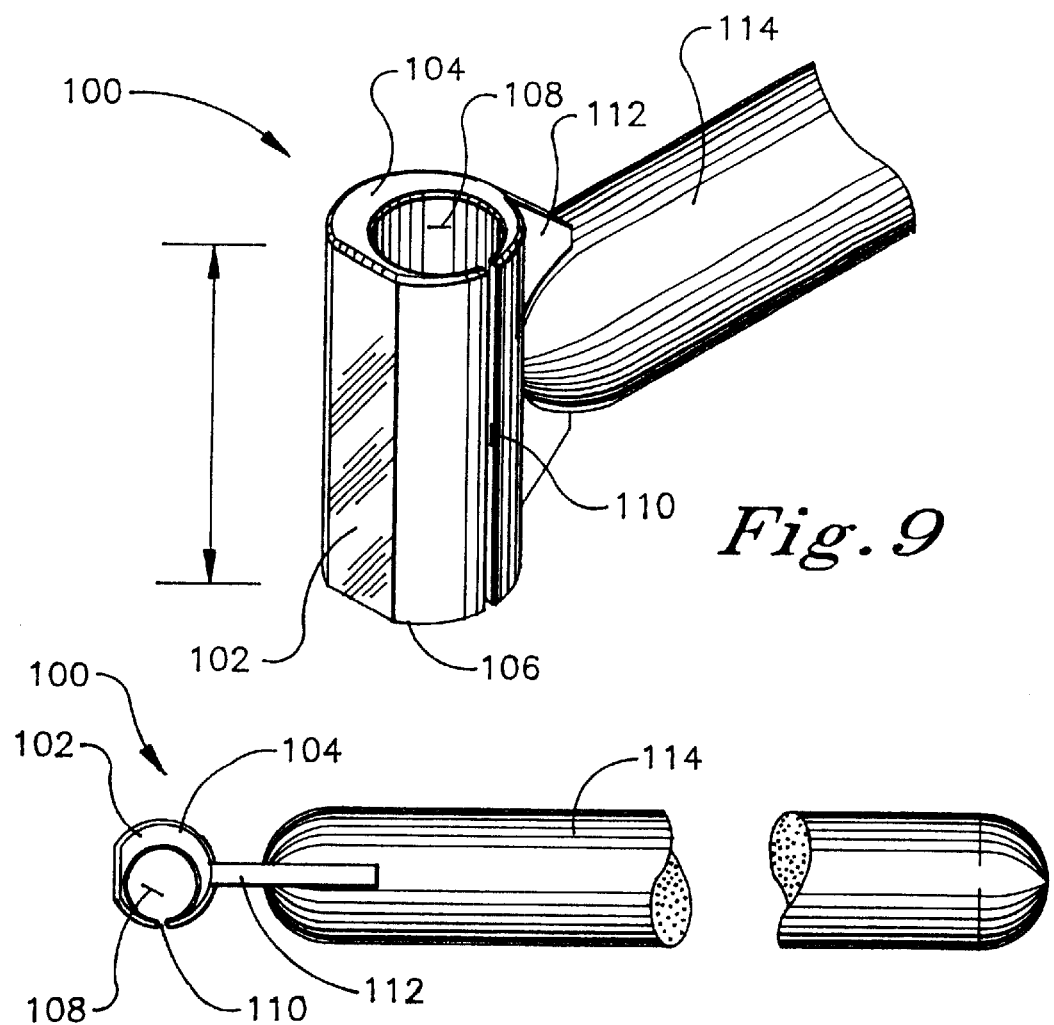

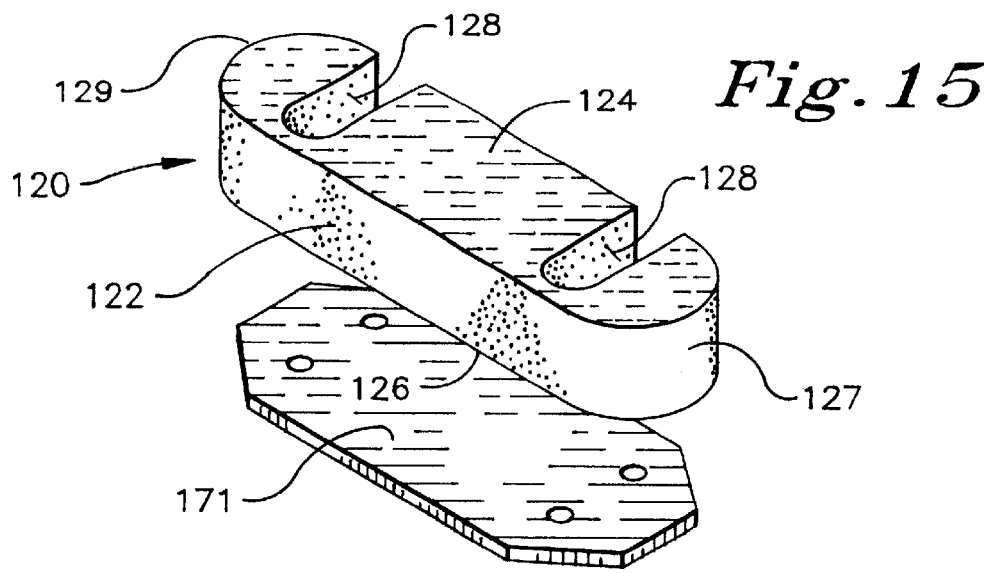
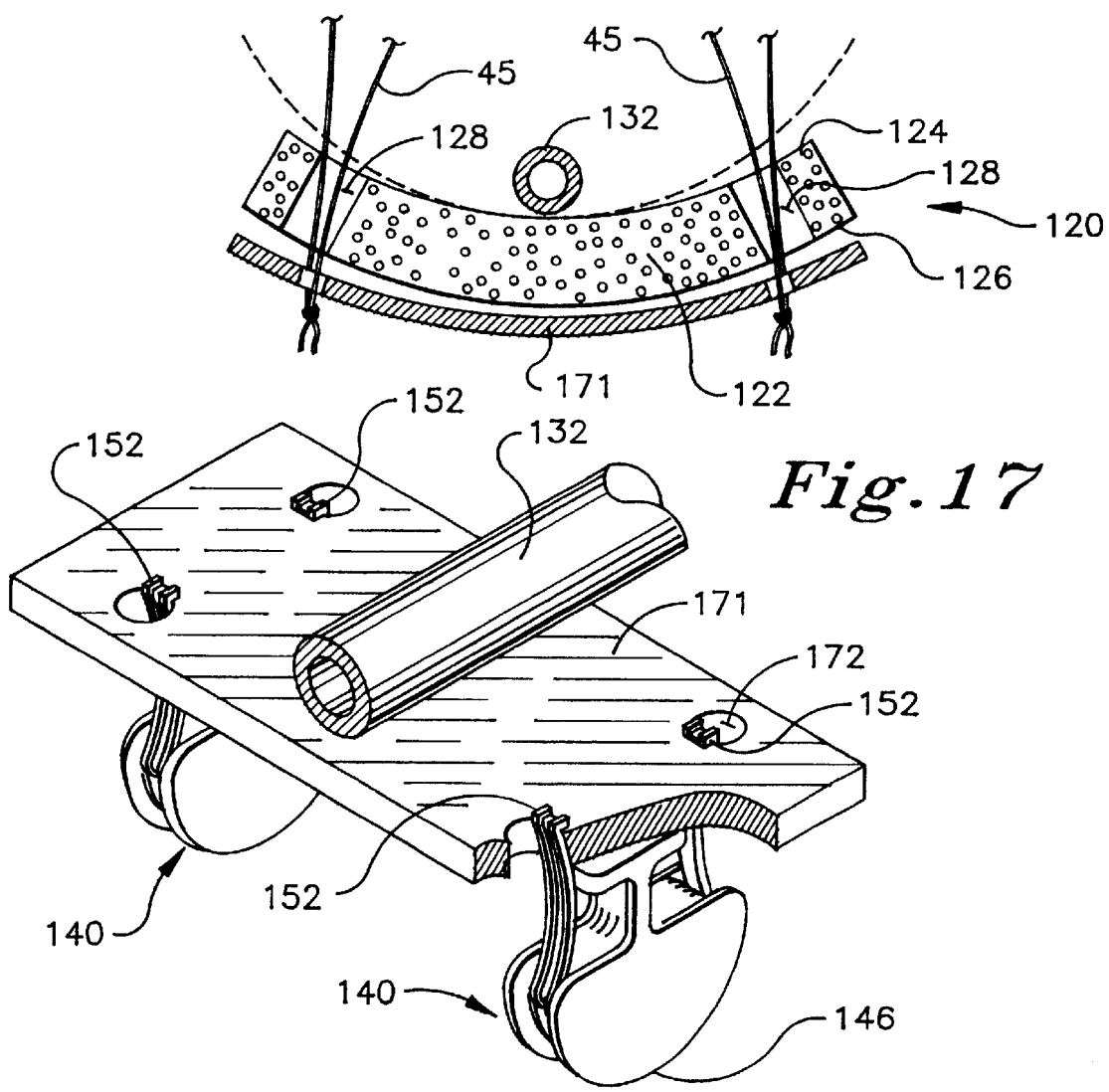

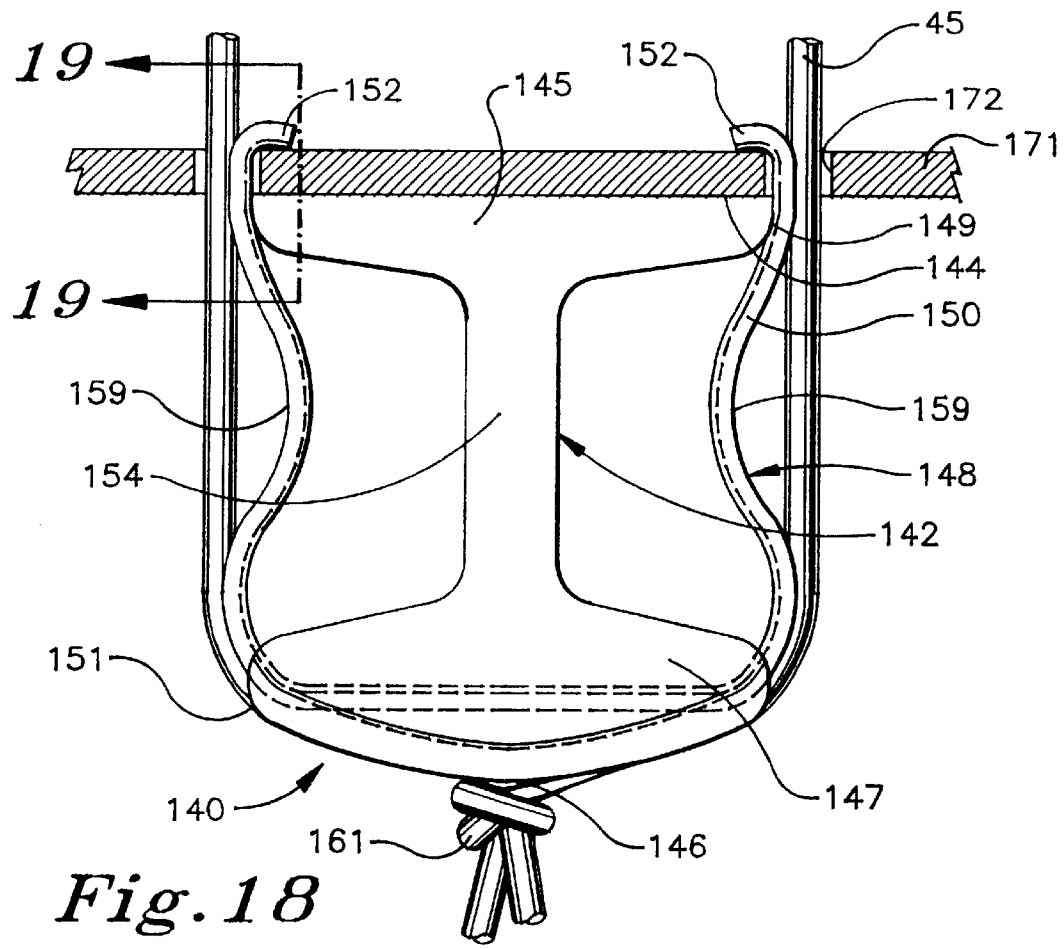
Fig.18
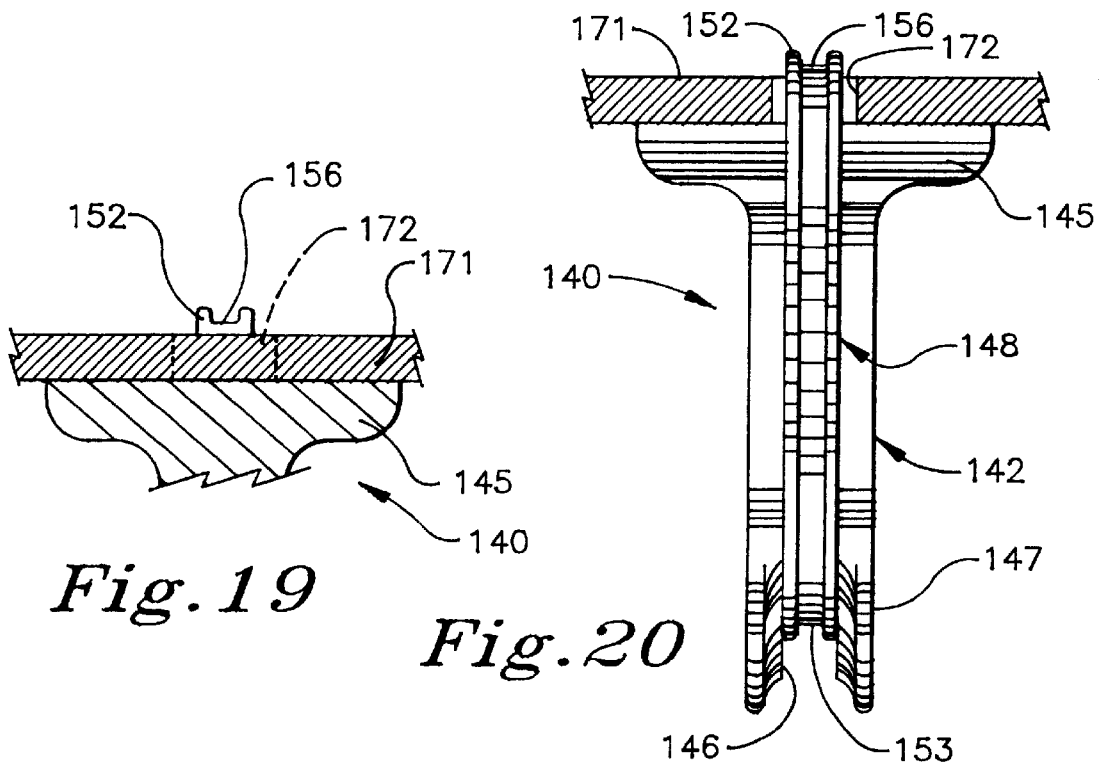
Fig.19
Fig.20

TRANSVAGINAL SUTURE SPACER DEVICES AND METHODS OF USE

RELATED APPLICATIONS

This application is a divisional application of U.S. patent application Ser. No. 09/184,468, filed Nov. 2, 1998.

TECHNICAL FIELD

The present invention relates to suture spacers and methods for their use. More particularly, the present invention relates to devices which permit a surgeon to create a consistent amount of suture slack in a suture line when tying sutures under very tight space constraints including procedures such as bladder neck stabilization and treatment of hypermobility or intrinsic sphincter deficiency. Further, the present invention relates to methods of tying sutures using the disclosed devices in such procedures.

BACKGROUND INFORMATION

Urinary incontinence is a widespread problem in the United States and throughout the world. Urinary incontinence affects people of all ages and can severely impact a patient both physiologically and psychologically.

In approximately 30% of the women suffering from urinary incontinence, incontinence is caused by intrinsic sphincter deficiency (ISD), a condition in which the valves of the urethral sphincter do not properly coapt. In approximately another 30% of incontinent women, incontinence is caused by hypermobility, a condition in which the muscles around the bladder relax causing the bladder neck and proximal urethra to rotate and descend in response to increases in intraabdominal pressure. Hypermobility may be the result of pregnancy or other conditions which weaken the muscles.

In addition, in an additional group of women with urinary incontinence, the condition is caused by a combination of ISD and hypermobility. In addition to the conditions described above, urinary incontinence has a number of other causes including birth defects, disease, injury, aging and urinary tract infection.

Numerous approaches for treating for urinary incontinence are available. For example, several procedures for stabilizing and/or slightly compressing the urethra so as to prevent leakage of urine have been developed. In one procedure, stabilizing or compressive force is applied directly by sutures passing through the soft tissue surrounding the urethra. Alternatively, the stabilizing or compressive force may be applied by means of a sling positioned between the urethra and the upper vaginal wall. In such procedures, sutures are secured to the sling and to a supporting structure in the body. Currently existing procedures may cause excessive pressure to be exerted on the bladder neck as a result of too little slack in the sutures.

Generally, procedures employing slings are performed with the patient in the dorsal lithotomy position. When the patient moves from the dorsal lithotomy position to a standing position the excessive pressure exerted on the bladder neck by the sling may result in chronic urinary retention or bladder instability.

Accordingly, there is a need for devices and procedures which ensure an appropriate and reproducible degree of slack in the sutures used to remedy the above mentioned disorders.

SUMMARY OF THE INVENTION

In one aspect, the invention relates to a suture spacer comprising a first member, a second member, and a border. The first member has a proximal end, a distal end, and a surface contacting side for contacting a suture emanating surface. The second member has a proximal end, a distal end, a surface contacting side for contacting suture emanating surface, and a knot formation side. The knot formation site is located on the knot formation side of the suture spacer. The border, and the distal ends of the first and second members define a suture receiving site for releasably receiving one or more sutures.

In another aspect, the invention features a suture spacer comprising a first member, a second member, and border. The first member has a proximal end and a distal end. The distal end of the first member also has a surface contacting side for contacting suture emanating surface and a knot formation side that is located generally opposite to the surface contacting side. The second member has a proximal end and a distal end with a surface contacting side for contacting suture emanating surface and a knot formation side located generally opposite to the surface contacting side. The border, and the distal ends of the first and second members define a suture receiving site for releasably receiving one or more sutures. The distance between the surface contacting sides and the knot formation sides of the first and second members defines a preselected amount of suture slack between suture emanating surface and a suture knot.

In another aspect, the invention features a suture spacer comprising a body having a surface contacting end, a knot formation end, a suture receiving lumen, and a slot. The surface contacting end may contact suture emanating surface. A suture knot maybe formed at the knot formation end. The suture receiving lumen extends from the surface contacting end to the knot formation end. The slot extends parallel to a longitudinal axis of the body. The slot is in fluid communication with the suture receiving lumen, and is adapted to releasably retain a suture within the suture receiving lumen. The distance from the surface contacting end to the knot formation end of the body and back again defines a preselected amount of slack in the suture when the suture spacer is used to form the suture knot.

In another aspect, the invention features a suture spacer comprising an elongate body having a surface contacting side, and a knot formation side. The surface contacting side can contact a suture emanating surface. A suture knot maybe formed at the knot formation end. The suture spacer has one or more suture receiving sites that extend between the surface contacting side and the knot formation side. The suture receiving sites are positioned to facilitate removal of the suture spacer after formation of the suture knot. The distance from the surface contacting side to the knot formation side and back again defines a preselected amount of suture slack.

In another aspect, the invention features a suture spacer comprising a body having a surface contacting side, a knot formation side, and an engagement member. The engagement member comprises an engagement body and at least one securing portion. The securing portion is movable between a first position in which the at least one securing portion and the surface contacting side engage the surface from which one or more sutures emanate and a second position in which the at least one securing portion releases the surface from which one or more sutures emanate.

In another aspect, the invention features a suture spacer comprising a shaft, a connector, and a slack defining member. The shaft has a proximal end and a distal end. The connector has a proximal end and a distal end. The proximal end of the connector is connected to the distal end of the shaft. The slack defining member is connected to the distal end of the connector. The slack defining member has a surface contacting side for contacting suture emanating surface and a knot formation side adjacent to which a suture knot is formed. The knot formation side of the slack defining member is disposed generally opposite to the surface contacting side. A preselected amount of suture slack is defined by a distance from the surface contacting side to the knot formation side and back again.

In another aspect, the invention features a method for producing a preselected amount of slack in a suture, comprising the steps of: transvaginally contacting a suture emanating surface with a suture spacer comprising a surface contacting side, a knot formation and a suture receiving site for releasably receiving the one or more sutures; inserting the one or more sutures emanating from the surface into the suture receiving site; tying a knot in the one or more sutures; and removing the suture spacer to produce the preselected amount of slack in the suture.

In another aspect, the invention features a method for producing a preselected amount of slack in a suture. The method comprises the following steps: contacting the suture emanating surface with a suture spacer comprising a shaft having a proximal end and a distal end, a connector, a slack defining member, and a knot formation side; tying a knot in the suture; and removing the suture spacer to produce the preselected amount of slack in the suture. The shaft is connected to the distal end of the connector having a proximal end and a distal end, the proximal end of the connector being connected to the distal end of the shaft. The slack defining member has a surface contacting side for contacting the suture emanating surface. The knot formation side is disposed generally opposite to the surface contacting side. A preselected amount of suture slack is defined by a distance from the surface contacting side to the knot formation side and back again.

BRIEF DESCRIPTION OF THE DRAWINGS

FIG. 9 is a perspective view of another embodiment of the suture spacer of the present invention.

FIG. 10 is a top view of the embodiment shown in FIG. 9.

FIG. 11 is a side view of the suture spacer shown in FIG. 9.

FIG. 15 is a perspective view of one embodiment of the suture spacer of the present invention and a sling used for improving urinary incontinence.

FIG. 16 is a cross-sectional view of the suture spacer depicted in FIG. 15 positioned between the female urethra and a sling which has been secured by knotting the sutures.

FIG. 17 is a perspective view of another embodiment of the suture spacer of the present invention engaged with a sling beneath the female urethra.

FIG. 18 is a front view of the suture spacer depicted in FIG. 17 secured to a sling.

FIG. 19 is a cross-sectional view of FIG. 18 taken along line 19—19.

FIG. 20 is a side view of the embodiment shown in FIG. 17.

DESCRIPTION

Figure 1:
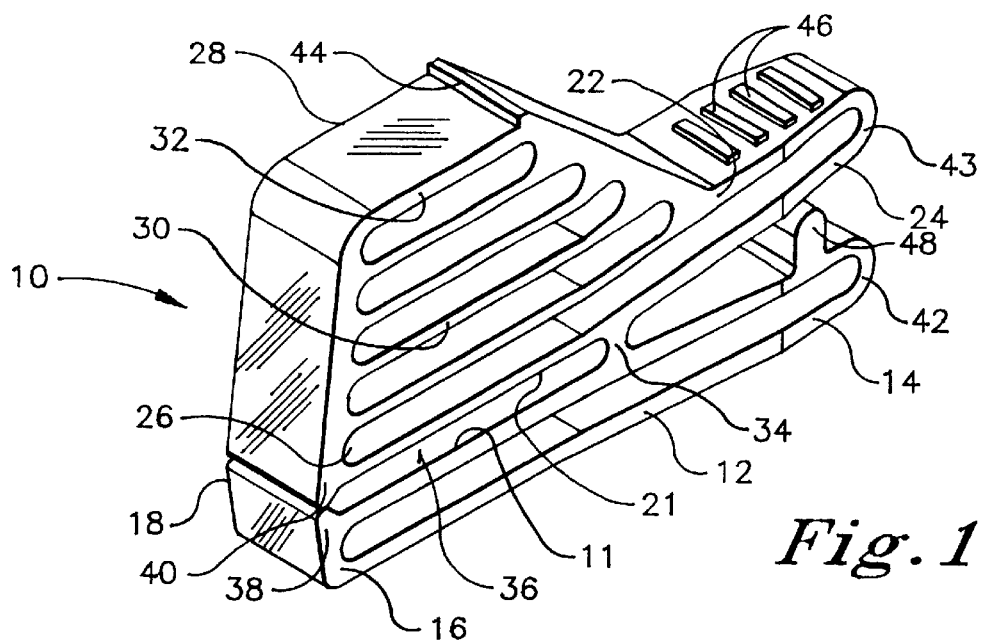
FIG. 1 is a perspective view of one embodiment of the suture spacer according to the present invention.

The present invention relates to apparatuses and methods for ensuring that a suture has a desired amount of slack. The present apparatuses and methods are particularly suited for use in bladder neck stabilization and/or suspension procedures. In such procedures the present invention provides a reproducible technique to produce a desired amount of suture slack when tying a suture used in a transvaginal surgical procedure, thereby avoiding chronic urinary retention and bladder instability.

The suture spacers disclosed herein provide consistent, repeatable amounts of slack in a suture which secures a sling or similar apparatus. The use of the present suture spacers minimizes post-operative urinary blockage caused by excessive tension, and minimizes post-operative urinary incontinence due to insufficient tension.

As used herein, the term "transvaginal" includes actions taken in the vaginal introitus or from within the vagina. The terms "proximal" and "distal" refer to points nearer to or further from the user of the device, respectively. The term "above" refers to the direction toward the abdomen of the patient, while the terms "below" or "under" refer to the direction toward the buttocks of the patient. The term "suture emanating surface" refers to a surface from which sutures emanate. This term includes slings and other such devices as well as tissues such as muscle or fascia from which sutures emanate. The term "pocket" refers to a surgical cavity created in the vagina. Sutures may also emanate from this surface. The term "hands-free manner" refers to the use of suture spacer where no additional assistance is required.

Generally, the suture spacers of the present invention are used to create slack in a suture as follows. A surface contacting side of a suture spacer is brought into contact with a surface from which one or more sutures emanate, such as a sling. A suture is introduced into a suture receiving site of the suture spacer and a suture knot is tied against a knot formation site on the suture spacer. In preferred embodiments of the suture spacers of the present invention, the suture spacer holds itself on the suture during use, thereby allowing the physician to use both hands to form the knot. In addition, this feature allows the suture spacer to be used without the aid of an assistant, thereby providing the physician with greater mobility at the surgical site. The surgical field remains free of obstacles which may hinder the suture securing phase of the surgery.

After a suture is introduced into the suture spacer, the suture ends are then brought together over the knot formation site and a knot is formed. The suture spacer is then removed from the patient, leaving a desired amount of slack in the suture. The amount of slack created by the suture spacer is determined as a function of the distance from a surface from which sutures emanate to the knot formation site or side of the suture spacer. The actual amount of slack created using the devices of the present invention will vary according to their size and shape. Also, the total amount of slack will be approximately twice the distance described above, as there are two lengths of which are tied together by the knot.

In one embodiment, the suture spacer comprises a first member which has a proximal end, a distal end, and a surface contacting side for contacting a surface from which one or more sutures emanate. This embodiment further comprises a second member also having a proximal end, a distal end, and a surface contacting side for contacting a surface from which one or more sutures emanate. The second member also has a knot formation side and a knot formation site located on the knot formation side. A border is disposed between the first and second members of the suture spacer such that the border, the distal ends of the first and second members of the suture spacer define a suture receiving site for releasably receiving suture. This embodiment creates a preselected amount of suture slack measured by the distance from the suture emanating surface to the knot formation site and back again.

Referring to FIG. 1, there is disclosed a perspective view of the suture spacer 10 of the present invention. The suture spacer 10 comprises a first member 12 having a proximal end 14, a distal end 16 and a surface contacting side 18.

The distal end 16 of the first member may have a protuberance 38 extending therefrom. The protuberance 38 may extend from the distal end 16 at an acute angle, an obtuse angle, or may be substantially perpendicular to the distal end 16 of the first member 12.

This embodiment of the suture spacer also has a second member 22 having a proximal end 24, a distal end 26, a surface contacting side 28, and a knot formation side 30. On the knot formation side of the second member 22, there is a knot formation site 32 upon which a knot is tied. Preferably, the knot formation site is located approximately in the center of the knot formation side 30 of the second member 22. The second member 22 may also have a suture retaining ridge 44, which holds the suture in place during knot tying.

The distal end 26 of the second member 22 may have a protuberance 40 extending therefrom. The protuberance 40 may extend from the distal end 26 of the second member 22 at an acute angle, an obtuse angle, or may be substantially perpendicular to the distal end 26.

The protuberances 38 and 40 may be flexible or rigid. In some embodiments, the protuberance 38 of the first member 12 and the protuberance 40 of the second member 22 contact each other.

The proximal ends 14 and 24 of the first member 12 and second member 22 may comprise handles 42 and 43. These handles 42 and 43 facilitate the movement of the first member 12 and second member 22 relative to each other. The handles also provide a means to grasp the suture spacer. The handles 42 and 43 shown have gripping ridges 46 to facilitate greater retention during manipulation.

Figure 3:
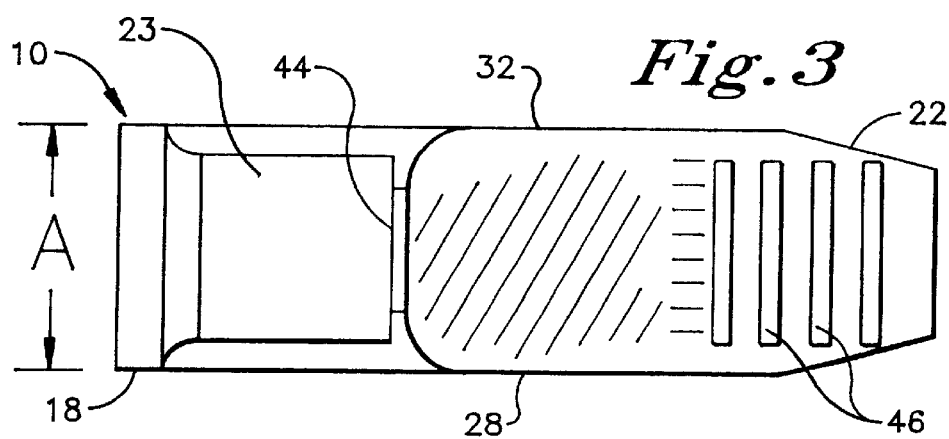
FIG. 3 is a side view of the suture spacer depicted in FIG. 1.

FIG. 3 shows a side view of suture spacer 10 which further includes a surface contacting side 18 on the first member 12. This Figure also shows the surface contacting side 28 and a knot formation side 32 on the second member 22.

Figure 2:
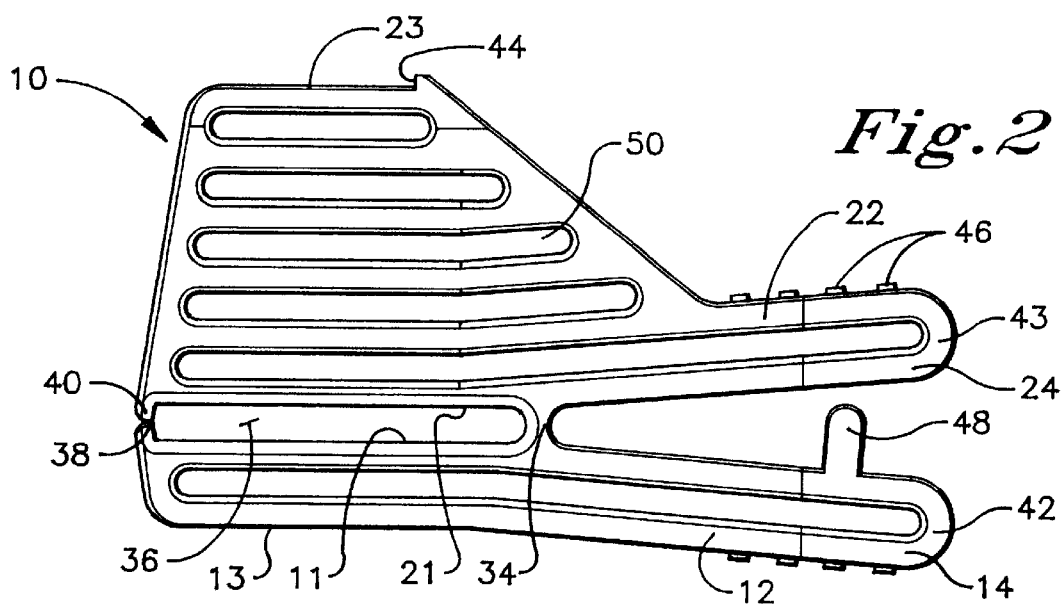
FIG. 2 is a top view of the suture spacer depicted in FIG. 1 in a closed position.

As shown in FIG. 2, the suture spacer can also have a border 34 disposed between the first member 12 and the second member 22. A suture receiving site 36 is defined by the border 34, and the protuberances of the first member 12 and second member 22, 38 and 40, respectively.

Alternatively, the suture receiving site 36 may defined by the border 34, and the distal ends 16 and 26. For example, distal ends 16 and 26 of first member 12 and second member 22 may meet to form a "V" which defines the distal end of the suture receiving site 36.

Figure 4:
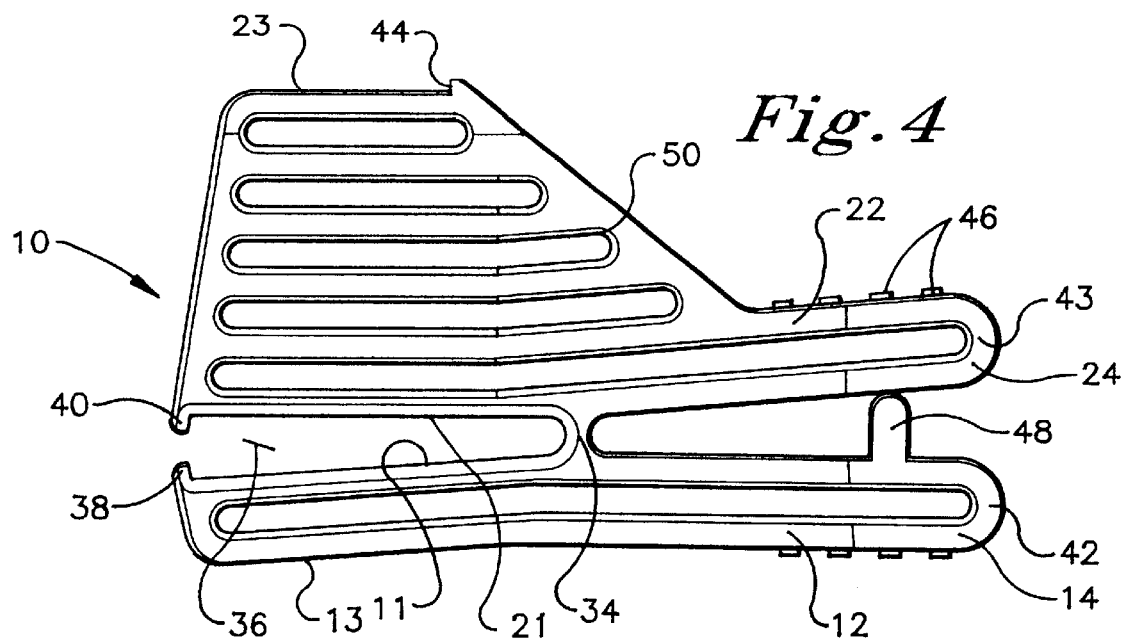
FIG. 4 is a top view of the suture spacer depicted in FIG. 1 in an open position.

As shown in FIG. 2, the first member may have a first side 11 and a second side 13. The second member may have a first side 21 and a second side 23. In one embodiment, the first member 12 and the second member 22 are movable with respect to each other to facilitate introduction of a suture into the suture receiving site 36. For example, the members may be movable with respect to each other through a hinge or pivot formed by border 34 positioned between a first side 11 of the first member 12 and a first side 21 of the second member 22. In this embodiment it is the movement of the two members 12 and 22 with respect to one another which permits a space to be formed between the protuberances 38 and 40 allowing the insertion of suture into the suture receiving site 36. The movement of the members to an open configuration is shown in FIG. 4 and the introduction of suture into this embodiment is discussed below. Suture entrance into the suture receiving site 36 requires a permanent or temporary gap between protuberances 38 and 40. Protuberances may be either rigid or flexible in a movable embodiments. In the non-movable embodiments, flexible protuberances could be used if they flex enough to permit entrance of suture into the suture receiving site 36. Similarly rigid protuberances could be used in a non-movable embodiment where there is a gap between the substantially rigid protuberances.

A limiting protuberance 48 may be disposed between the first member 12 and second member 22 to limit their mobility of the two members. The limiting protuberance 48 may be included on either member, or may be omitted entirely.

In another embodiment, the two members do not move with respect to each other. In such a non-moving embodiment, the protuberances 38 and 40 are made of a flexible material. The flexible material of the protuberances serves to permit the introduction of a suture between them as a function of their flexibility. In this embodiment, preferably the suture spacer 10 is held stationary and a suture is introduced into the suture receiving site 36 by forcing the suture against the protuberances 38 and 40. The force of the suture pressing against the flexible protuberances causes them to bend towards the suture receiving site 36, creating a gap through which the suture can enter the suture receiving site.

Alternatively, the suture may be held stationary while the suture spacer 10 is forced over it to introduce the suture into the suture receiving site 36. Also, it is contemplated that both the suture and the suture spacer 10 may be moved against each other so as to introduce suture into suture receiving site 36.

Once the suture has passed through the gap, the flexible protuberances 38 and 40 return to their original position, closing the gap and enclosing the suture in the suture receiving site 36. A suture knot is then tied at the knot formation site 32. After a suture knot has been formed, the suture may be removed from the suture receiving site 36 by again forcing the suture against the flexible protuberances 38 and 40 and creating a gap through which the suture can exit the suture receiving site 36.

Casting grooves 50 shown in FIG. 2 may also be included in the spacer to facilitate plastic casting of the embodiment. The grooves increase moldability and reduce warpage.

With respect to dimensions, the suture spacer 10 has the appropriate dimensions to facilitate its use as a means to reproducibly create a predetermined amount of suture slack when used in a surgical procedure. Accordingly, the length of the first member 12 and second member 22 may vary. In one embodiment the members may have an axial length from about 0.1 to 12.0 inches in length. In another embodiment the members may have an axial length from about 0.5 to 6.0 inches in length. In still another embodiment, the members may have an axial length of about 1.0 to 3.0 inches. In a highly preferred embodiment, the first member 12 and the second member 22 have axial lengths of about 1.35 inches.

The amount of predetermined suture slack is partially determined by the distances between the surface contacting side 28 and the knot formation site 32 of various embodiments of the present invention will also vary. Shown as A in FIG. 3, the distance from the surface contacting side 28 to the knot formation site 32 is from about 0.01 to 5.0 inches in length. In another embodiment the distance between the surface contacting side 28 and the knot formation site 32 is from about 0.1 to 2.5 inches in length. In a highly preferred embodiment, the distance between the surface contacting side 28 and the knot formation site 32 is about 0.275 inches.

The amount of predetermined suture slack is also determined by the dimensions of the second member 22 on which the knot formation site 32 resides. The second member 22 of the suture spacer 10 shown in FIG. 2 further comprises a first side 21 and a second side 23 which further defines the borders of the second member 22. In one embodiment, the distance from the first side 21 to the second side 23 of the second member 22 is from about 0.001 to 10 inches. In another embodiment, the distance from the first side 21 to the second side 23 of the second member 22 is from about 0.01 to 1.0 inches. In a highly preferred embodiment, the distance from the first side 21 to the second side 23 of the second member 22 is about 0.525 inches.

The length of the suture receiving site 36 is determined by the distance from the border 34 to the distal ends 16 and 26 of the first member 12 and second member 22. In one embodiment the length of suture receiving site 36 is from about 0.001 to 5 inches. In another embodiment the length of suture receiving site 36 is from about 0.01 to 2.5 inches. In still another embodiment the length of suture receiving site 36 is from about 0.1 to 1 inch. In a highly preferred embodiment, the length of suture receiving site 36 is about 0.688 inches long when measured from the distal ends 16 and 26 of the first member 12 and second member 22.

The width of the suture receiving site 36 is determined by the distance from the first side 11 of the first member 12 to the first side 21 of second member 22. In one embodiment, the suture receiving site 36 is from about 0.001 to 1.0 inch wide. In another embodiment, the suture receiving site 36 is from about 0.01 to 0.5 inches wide. In a highly preferred embodiment, the suture receiving site 36 is about 0.06 inches wide when measured from the first side 11 to first side 21 of the first and second members, 12 and 22, respectively.

The protuberances 38 and 40 shown in FIG. 2 are from about 0.005 to 0.5 inches in length and width. In another embodiment, the protuberances are from about 0.001 to 0.25 inches in length and width. In still another embodiment, the protuberances are from about 0.01 to 0.125 inches in length and width. In a highly preferred embodiment, the protuberances are about 0.03 inches in length and width. Protuberances 38 and 40 may extend from their respective members at a substantially acute angle, a substantially obtuse angle, or at a substantially perpendicular angle.

In one embodiment, the handles 42 and 43 are from about 0.05 to 5.0 inches wide and extend away from a central axis through the suture receiving site 36 at an angle from about 2.5° to 25.0°. In another embodiment, the handles 42 and 43 are from about 0.1 to 1.0 inches wide and extend away from a central axis through the suture receiving site 36 at an angle from about 5.0° to 15.0°. In a highly preferred embodiment, the handles 42 and 43 are about 0.15 inches wide and extend away from a central axis through the suture receiving site 36 at an angle of about 9.5°.

In another highly preferred embodiment, the gripping ridges 46 are about 0.01 inches high and about 0.03 inches wide, with the ridges set about 0.05 inches apart from each other.

In a highly preferred embodiment, the limiting protuberance 48 is about 0.06 inches wide and is positioned about 0.42 from the proximal side of the border 34.

In a highly preferred embodiment, the height of the suture retaining ridge 44 is about 0.02 inches and the ridge is set away from the distal end of the second member by about 0.456 inches.

The above described embodiment is only one possible configuration of the present invention. Other configurations will also become apparent to one of skill in the art in view of the present disclosure. Suture spacer 10 may be constructed in any of a variety of ways which will be well understood by one of skill in the art of constructing medical devices, such as by injection molding. A highly preferred embodiment of suture spacer 10 shown in FIG. 1 is constructed from acrylonitrile butadiene styrene resin (ABS), but other materials contemplated include but are not limited to thermoplastic elastomers, polyethylene, polypropylene, polycarbonate, nylon, rubber material, other plastics and stainless steel.

Example 1 describes the use of the suture spacer in a transvaginal bladder neck stabilization procedure in which the stabilization or compression is achieved by a sling.

EXAMPLE 1

The suture spacers of the present invention such as suture spacer 10 may be used in incontinence treatments in which the urethra and/or bladder neck is compressed or stabilized using a sling. In such procedures the sling may be secured to the vaginal wall through sutures attached to structures which are of sufficient structural integrity so as to support the forces exerted in the region. For example, suitable structures include the pubic bone, ligaments or appropriate muscle groups adjacent to the bladder neck or urethra.

Preoperatively, the patient receives broad spectrum antibiotics, such as gentamicin and ampicillin. The patient is placed in the dorsal lithotomy position and regional or general anesthesia is administered. Preparation of the patient emphasizes isolation of the anus with a stapled towel or plastic drape. A Foley catheter is inserted into the urethra to indicate its location.

Starting adjacent to the bladder neck on either side of the urethra, a 1 cm incision is preferably made through the anterior vaginal wall approximately 1 cm lateral to and parallel to the midline of the urethra. The vaginal wall is retracted to allow access to the endopelvic fascia. The surgeon then inserts an instrument such as surgical scissors through the incision in the upper vaginal wall and bluntly dissects the tissue under the urethra to create a bilaterally extending pocket.

Alternatively, the bilaterally extending pocket can also be created and the sling can be inserted using a variety of other minimally invasive instruments/methods including the transvaginal, hiatal and percutaneous approaches disclosed in the pending U.S. patent application entitled "Percutaneous and Hiatal Devices and Methods for Use in Minimally Invasive Pelvic Surgery" Ser. No. 09/023,965, and the pending U.S. patent application entitled "Method and Apparatus for Minimally Invasive Pelvic Surgery" Ser. No. 09/023,533, the disclosures of which are hereby incorporated herein by reference.

Bone anchor implantation devices such as those disclosed in the pending U.S. patent application entitled "Transvaginal Anchor Implantation Device" Ser. No. 08/744,439, the disclosure of which is hereby incorporated herein by reference, may be used to implant bone anchors into a suitable structure such as the pubic bone as described therein.

Briefly, the bone anchor implantation device is introduced through the opening in the vaginal wall. Preferably, two bone anchors are used, although the use of one bone anchor is contemplated. The first anchor implantation site is preferably located lateral to the symphysis pubis and cephalad to the inferior edge of the pubic bone. More preferably, the first anchor implantation site is located approximately 1 cm lateral to the symphysis and 1 cm cephalad to the inferior edge of the pubic bone. Bone anchors having sutures attained thereto are implanted into the pubic bone as described in pending U.S. patent application Ser. No. 08/744,439. Once the anchor is preferably driven into the pubic bone using manual pressure, the bone implantation device is withdrawn leaving the two free ends of suture exiting the endopelvic fascia.

The above bone anchor implantation procedure is preferably repeated to introduce a second anchor on the same side of the urethra as the first anchor. The second anchor implantation site is located by palpating the obturator foramen in the pelvis just cephalad to the ramus. For implantation of the second anchor, the fascial tissue near the proximal end of the vaginal wall incision farther from the bladder neck is pierced. The second anchor is implanted on the superior (cephalad) aspect of the ramus.

The bone anchor implantation device is removed as before trailing the two free ends of each suture from the vaginal wall incision.

The above procedure for implantation of the first and second anchors are repeated on the opposite side of the urethra.

The surgeon selects a sling and places it into the pocket. The sling may be introduced into the pocket using the devices and methods disclosed in U.S. application Ser. Nos. 09/023,965 and 09/023,533 the disclosures of which are hereby incorporated by reference. The sling may comprise the slings disclosed in the U.S. patent application entitled, "Stabilization Sling for use in Minimizing Evasive Pelvic Surgery" Ser. No. 09/023,398, the disclosure of which is incorporated herein by reference. The sling is placed in the tissue between the urethra and the upper vaginal wall, preferably under the bladder neck.

As will be apparent to one of skill in the art, the sling may be placed beneath the urethra and/or bladder neck in a variety of ways other than via a pocket. For instance, an inverted U shaped incision may alternatively be made beneath the bladder neck. The tissue beneath the inverted U shaped incision may be bluntly dissected to create a flap. The sling may then be inserted in the dissected opening.

After placing the sling in the pocket or opening, the surgeon aligns the sling so that it is located directly beneath the urethra and/or bladder neck. As will be apparent to one of skill in the art, alignment of the sling relative to the urethal and/or bladder neck can be accomplished in a variety of ways, such as by direct visualization.

Figure 1A:
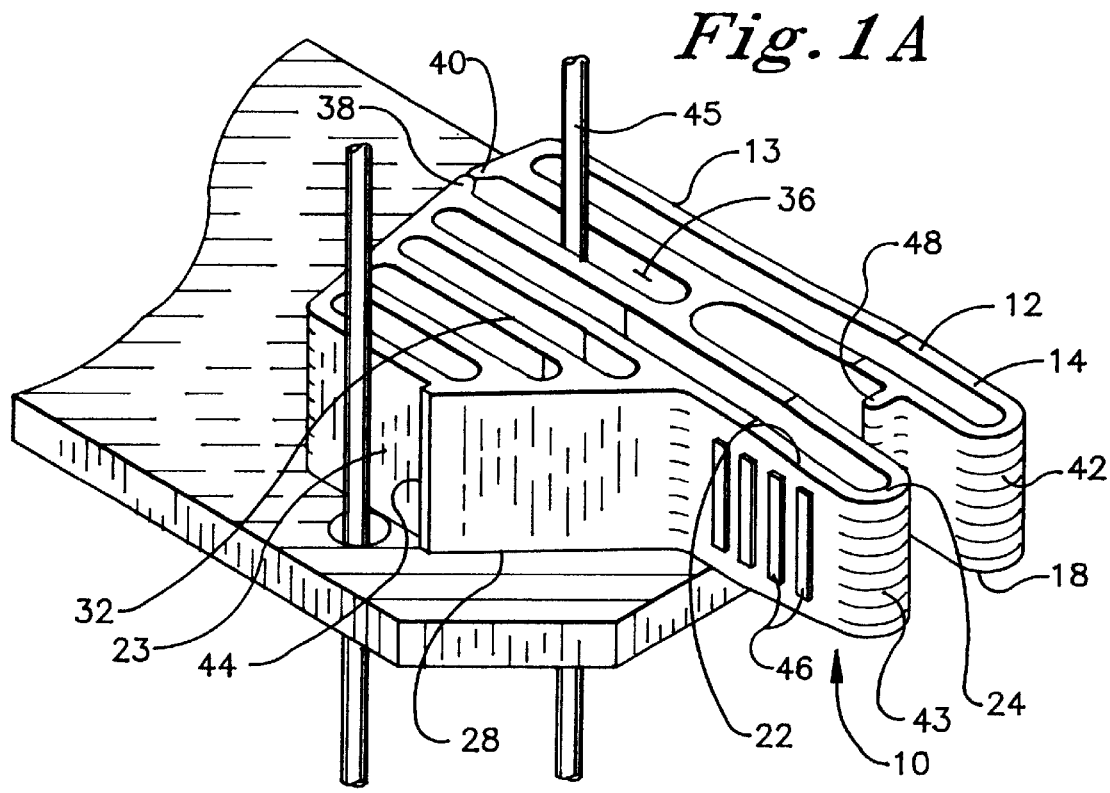
FIG. 1A is a perspective view of the suture spacer depicted in FIG. 1 positioned adjacent to a sling.

After the sling is correctly positioned, the ends of the sutures are passed through suture receiving sites, such as apertures, in the sling such that the ends of the sutures extend past the underside of the sling. Alternatively, the sutures may be preattached to the sling. Next, a suture spacer such as suture spacer 10 illustrated in FIG. 1A, is placed on its side, such that the surface contacting sides 18 and 28 of the first member 12 and second member 22 contact the sling.

Suture 45 may be introduced into the suture spacer 10 by applying and maintaining a quantity of force against the proximal ends 14 and 24 of the first member 12 and second member 22. With sufficient force the distal ends of the first and second members are moved away from each other, creating a gap between those ends. FIG. 4 shows the position of the first member 12 and the second member 22 when such force is applied. Suture is introduced into the suture receiving site 36 after the first member 12 and second member 22 separate. Alternatively, suture may be introduced into a non-moving embodiment of the present invention using the method described above.

Following introduction of the suture, the force applied against the first and second members 12 and 22 is removed and those members return to their position immediately adjacent to each other. In returning to their original position, the first and second members enclose the suture in the suture receiving site 36.

Once suture spacer 10 has enclosed the suture, the movement of the spacer is limited to sliding on the suture itself. Movement of suture spacer 10 may be further limited by looping the ends of the suture about each other over the device. Limiting the movement of the suture spacer 10 in the surgical field eliminates the need of additional assistance, which could obscure the surgical field.

Referring to FIG. 1A, the first end of suture 45 is then introduced into the suture receiving site 36. Sutures used in this method may vary according to practices known by those of skill in the art. An example of a suitable suture type would be a suture made of a braided polyester. The surgeon then applies an appropriate amount of tension to the sutures. Appropriate tensioning of the sutures may be visually confirmed by looking at tissue movement about the urethra. Tension off the suture/sling should be minimal. With the patient in the dorsal lithotomy position, the tension should be acceptable when the bladder neck is snugged but not elevated. This will create a "floor" against downward mobility during micturition. Alternatively, the internal diameter of the urethra may be visualized with a cystoscope. A reduced internal diameter indicates the presence of appropriate tension. The suture ends are then secured together by tying the first and second ends of the sutures across the suture spacer 10 adjacent to the knot formation site 32. A predetermined amount of suture slack is formed as measured by the distance from the point where the suture first emanate from the body, up through the sling, on to the suture spacer 10, and over to the knot formation site. Since there are preferably two sutures for each knot, the total amount of slack created through use of the suture spacers disclosed herein will be about twice the distance of the path described above. The suture spacer is thereafter removed from the suture using the steps described above and the procedure is repeated until all the sutures have been secured. In all embodiments, the suture spacer may be placed on either the same side or the opposite side as the knot. In embodiments using a sling, the suture spacer may be used either above or below the sling.

After the suture spacer has been removed, the incisions in the vaginal wall are closed. Following closure, the wounds are irrigated with an antibiotic solution, such as a bacitracin solution. The wound edges and the rectus fascia at the suture entry points may be infiltrated with an anesthetic such as bupivacaine. A new Foley catheter may be introduced. Alternatively, a suprapubic tube can be placed, especially in those patients having dexterity problems or an aversion to learning intermittent catheterization.

Following surgery, the patient is given an antibiotic such as either ciprofloxacin or ofloxacin for ten days. For those patients having a Foley catheter, the catheter is removed approximately one week following surgery. The patient performs intermittent catheterization as necessary until the post-void residuals are less than 75 cc on two consecutive catheterizations. In patients having a suprapubic tube, the suprapubic tube is removed when the post-void residuals are less than 75 cc following two consecutive urinations.

In another embodiment, the suture spacer comprises a first member, a second member and a border. The first member includes a proximal end and a distal end defining the length of the device. The distal end of the first member comprises a surface contacting side for contacting a surface from which one or more sutures emanate and a knot formation side generally opposite to the surface contacting side of the first member.

The second member of this embodiment comprises a proximal end and a distal end. The distal end of the second member includes, a surface contacting side for contacting a surface from which one or more sutures emanate and a knot formation side generally opposite to the second surface contacting side.

This embodiment also has a border disposed between the first and second members. The border, together with the distal ends of the first and second members create a suture receiving site for releasably receiving a suture. The desired amount of suture slack created by this embodiment is measured by the distance from a suture emanating surface to the first and second knot formation sides and back again.

Figure 5:
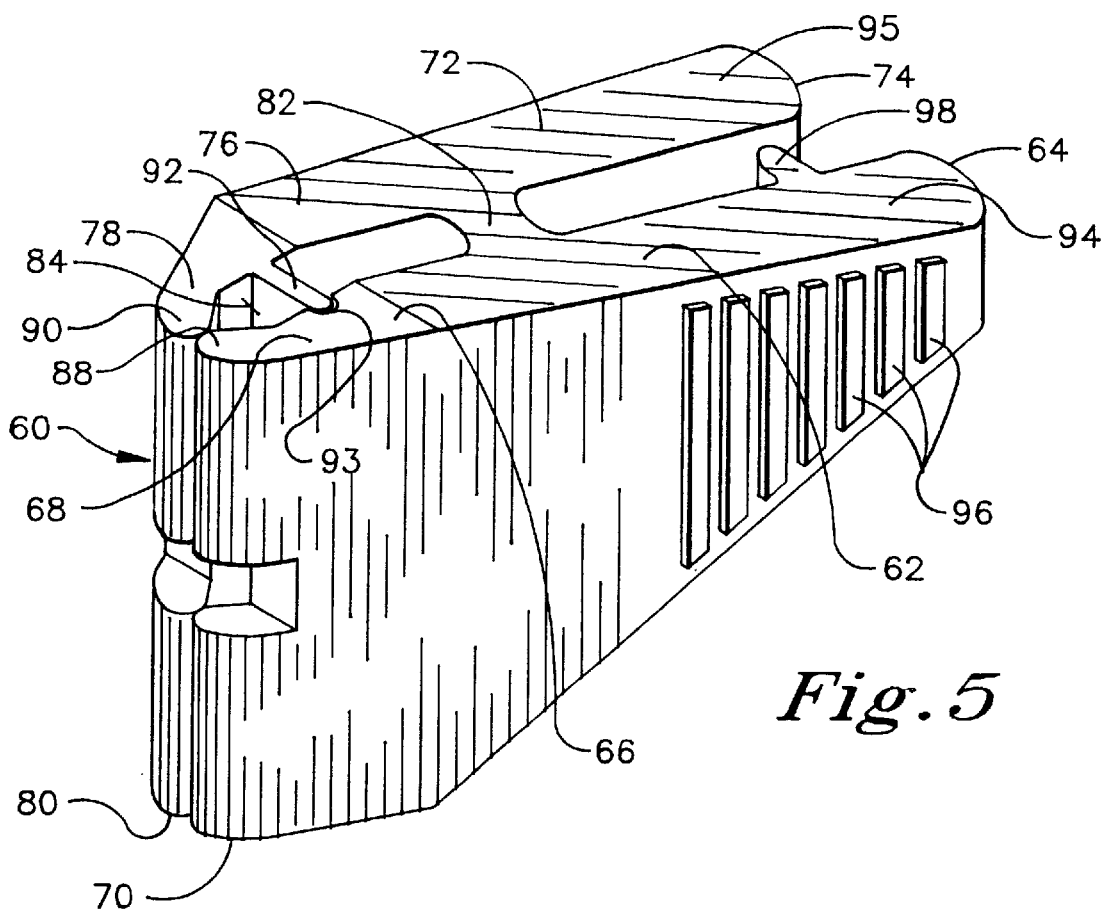
FIG. 5 is a perspective view of another embodiment of the suture spacer of the present invention.
Figure 6:
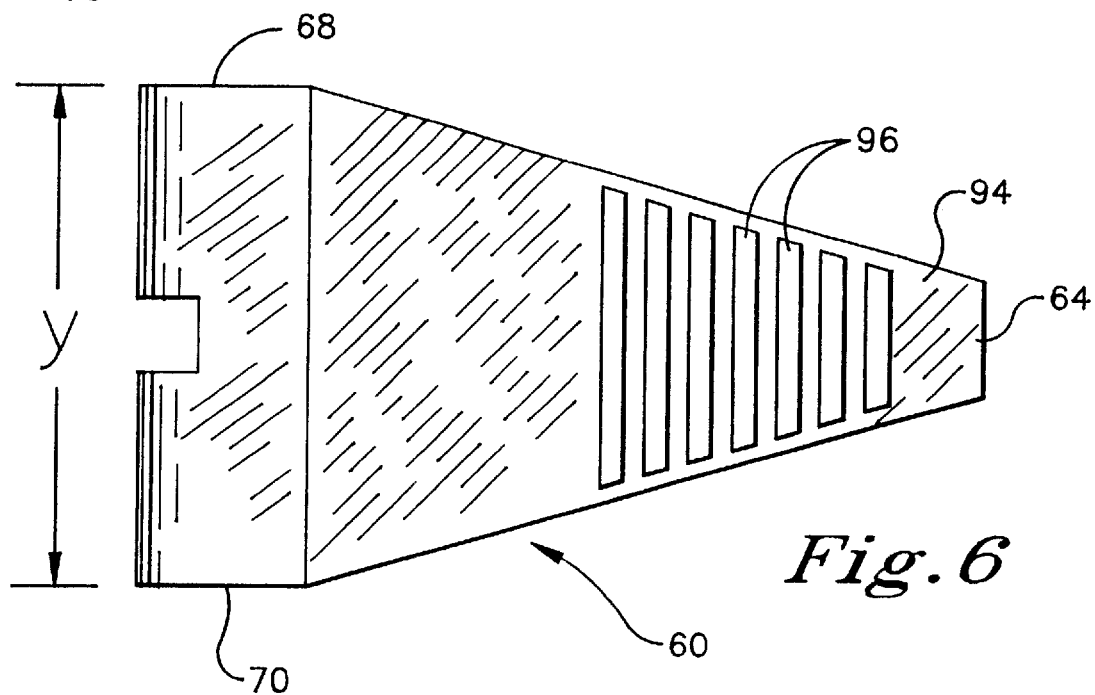
FIG. 6 is a side view of the suture spacer depicted in FIG. 5.

FIGS. 5 through 8 show an embodiment suture spacer of the present invention. Referring to FIG. 5, there is disclosed a perspective view of the suture spacer 60. This embodiment includes a first member 62 having a proximal end 64 and a distal end 66. The distal end 66 further comprises a surface contacting side 68 and a knot formation side 70 disposed on the opposite side of the suture spacer 60 from the surface contacting side of the first member 62. In a preferred embodiment, the surface contacting side 68 and knot formation side 70 of distal end 66 are disposed parallel to each other. FIG. 6 shows the position of first surface contacting side 68 relative to first knot formation side 70.

As illustrated in FIG. 5 the suture spacer 60 further comprises a second member 72 which has a proximal end 74 and a distal end 76. The distal end 76 further comprises a surface contacting side 78 and a knot formation side 80 disposed on the opposite side of the suture spacer 60 from the surface contacting side 78. The amount of slack created by suture spacer 60 is determined by the distance between the surface contact sides 68 and 78 and the knot formation sides 70 and 80. This distance is defined by suture slack defining distance Y as shown in FIG. 6.

Suture spacer 60 further comprises a hinge or pivot 82 disposed between the first and second members 62 and 72.

The proximal ends 64 and 74 may also comprise handles 94 and 95. Pressure upon the handles in the present embodiment results in movement of the two members away from each other, allowing the introduction of suture therebetween. In one embodiment, the handles may have gripping ridges 96 which assist in manipulation of the device during use.

In one embodiment, the first member 62 is movable with respect to the second member 72 so as to create a gap between the first member 62 and the second member 72 through which a suture can be introduced into the suture receiving site 84. For example, the first and second members 62 and 72 may be movable with respect to each other through a hinge or a pivot 82 positioned between proximal and distal ends of the first and second members.

Figure 7:
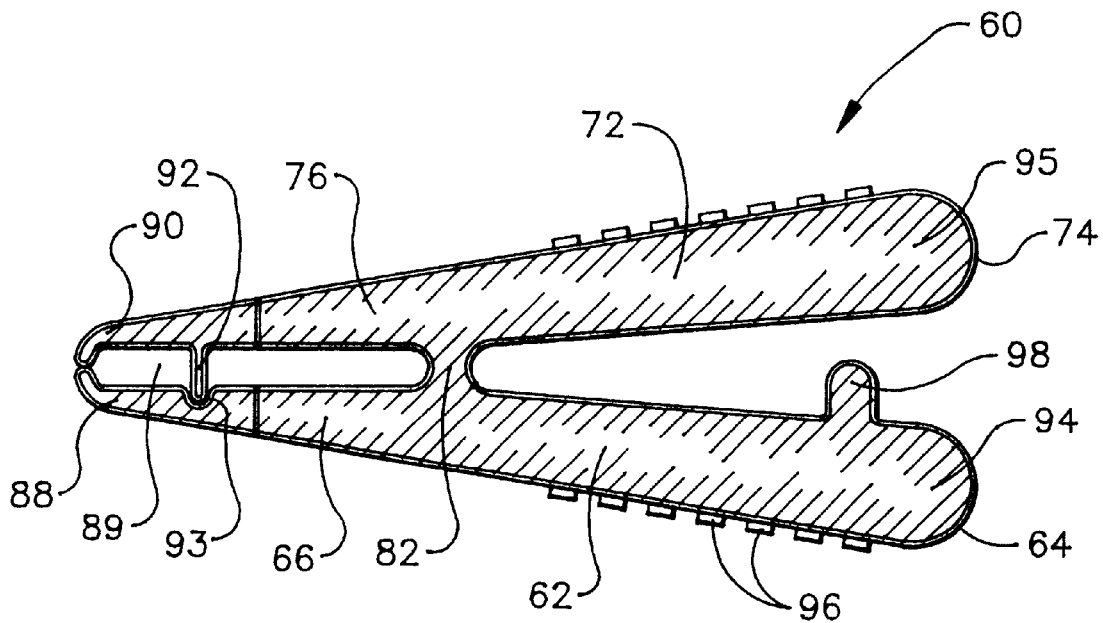
FIG. 7 is a top view of the suture spacer depicted in FIG. 5.
Figure 8:
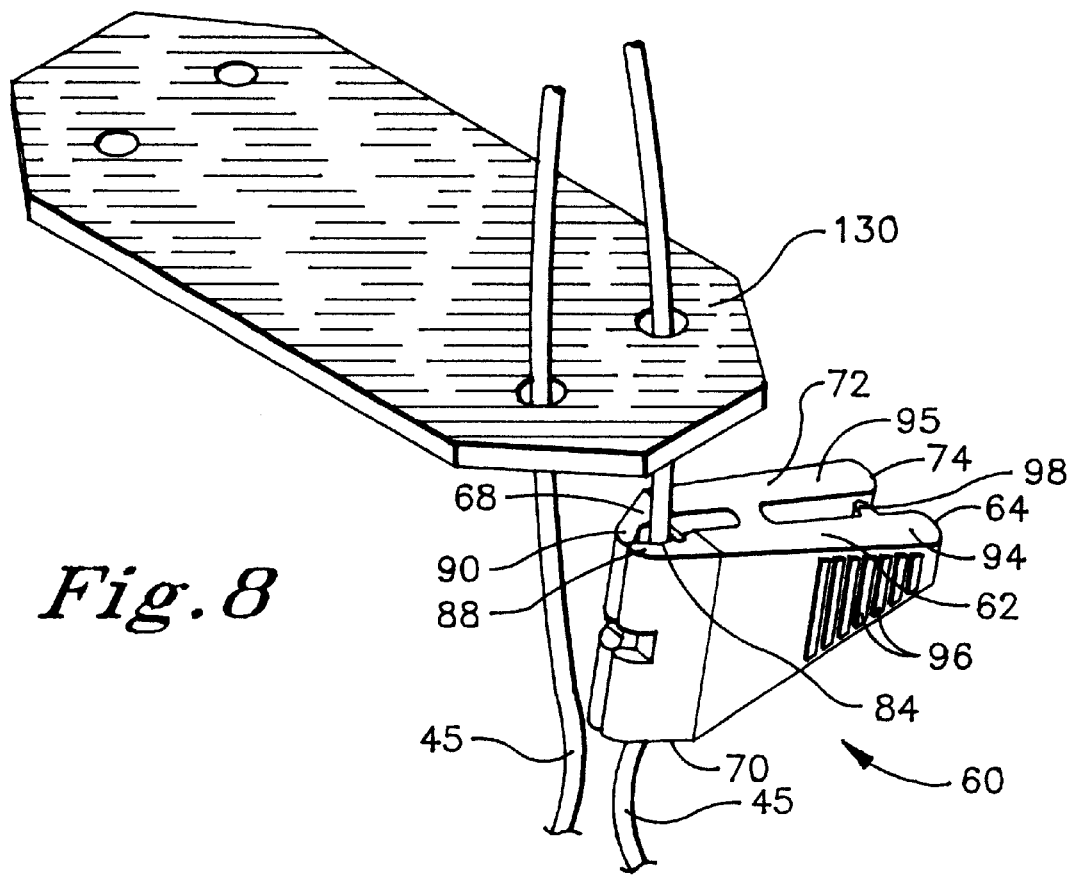
FIG. 8 is a perspective view of the suture spacer depicted in FIG. 5 with a length of suture in its suture trapping groove and through the suture receiving site on a sling used for improving urinary continence.

As illustrated in FIGS. 5 and 7, the distal end 66 of the first member 62 may comprise a protuberance 88. The distal end 76 of the second member 72 may also comprise a protuberance 90. The distal ends 66 and 76 of the first and second members 62 and 72 serve to retain a suture introduced into the suture receiving site 84. The protuberances may be substantially rigid or substantially flexible. As illustrated in FIGS. 7 and 8, the border 92 and border groove 93 can define a suture trapping groove 89. Substantially flexible protuberances can be used to allow the introduction of suture into the suture receiving site 84, such as in embodiments which permit no movement between the first member 62 and the second member 72.

In an embodiment in which movement between the two members 62 and 72 is permitted, rigid or flexible protuberances may be used. The introduction of suture into this embodiment is discussed below. Protuberances 88 and 90 may extend from their respective members at a substantially acute angle, a substantially obtuse angle, or at a substantially perpendicular angle. Alternatively, rigid protuberances could be used if a gap was left between substantially rigid protuberances.

The embodiment shown in FIG. 7 the suture spacer may also include a border 92 which is disposed between the first and second members, 62 and 72. In the illustrated embodiment, a border groove 93 is also present and serves to accommodate border 92. In other embodiments, the border 92 may be absent and the suture receiving site 84 may be defined by the hinge or pivot 82 and the first and second distal ends 66 and 76.

As shown in FIG. 7, some embodiments of suture spacer 60 may have a limiting protuberance 98 disposed between the first and second members, 62 and 72, respectively. The function of the limiting protuberance 98 is to limit movement between the first and second members.

Referring to FIG. 7, suture may be introduced into the suture spacer 60 by applying and maintaining a quantity of force against the proximal ends 64 and 74, of the first and second members 62 and 72, respectively. With sufficient force the distal ends 64 and 74 of the first and second members 62 and 72 are moved away from each other, creating a gap between those ends. Suture is introduced into the suture receiving site 84 after the first and second members 62 and 72 separate.

Following introduction of the suture, the force applied against the first and second members, 62 and 72, is removed and those members return to their original position immediately adjacent to one another. In returning to their original position, the first and second members, 62 and 72, enclose the suture in the suture receiving site 84. The ends of suture are then drawn together and a suture knot is tied on the knot formation sides 70 or 80. The knot formation side used in the knot tying procedure will depend on which side the knot is tied. After a suture knot has been formed, the suture may be removed from the suture receiving site 84 by following the steps described above.

In some embodiments, the first member 62 and the second member 72 are not movable with respect to each other. In this non-moving embodiment, the protuberances 88 and 90 are made of a flexible material which permits the introduction of a suture between them as a function of their flexibility. Preferably, in such an embodiment, the suture spacer 60 is held stationary and a suture is introduced into the suture receiving site 84 by forcing the suture against the protuberances 88 and 90. The force of the suture pressing against the flexible protuberances causes them to bend, creating a passage past the distal ends 66 and 76 of the first and second members 62 and 72 to the suture receiving site 84. Alternatively, the suture may be held stationary while the suture spacer 60 is forced over it to introduce the suture into the suture receiving site 84. Also, it is contemplated that both the suture and the suture spacer 60 may be moved against each other to introduce suture into suture receiving site 84.

Once the suture has entered the suture receiving site 84, the flexible protuberances 88 and 90 return to their original position, closing the passage and enclosing the suture into the suture receiving site 84. A suture knot is then tied using the suture spacer 60 to define a predetermined amount of slack. After a suture knot has been formed, the suture may be removed from the suture receiving site 84 by again forcing the suture against the flexible protuberances 88 and 90 and creating a gap between the first and second members 62 and 72.

With respect to the dimensions of this embodiment of the present invention, the length of the present invention is determined by the distance from the proximal to the distal ends. In one embodiment of the present invention the suture spacer 60 measures from about 0.1 to 5 inches in length. In another embodiment of the present invention the suture space 60 measures from about 0.5 to 2.5 inches in length. In highly preferred embodiment, suture spacer 60 measures about one inch in length from the most proximal end to the center of the suture receiving site 84.

In a highly preferred embodiment, the V-shape of the first and second members 62 and 72 extend from a base at about 18°. In this highly preferred embodiment, the height of the handles is about 0.145 inches at the most proximal point of either member.

In one embodiment of the present invention, the slack defining distance Y ranges from about 0.1 to 5.0 inches. In another embodiment of the present invention, the slack defining distance Y ranges from about 0.5 to 1.0 inches. In a highly preferred embodiment, the distance Y, shown in FIG. 6, is about 0.625 inches.

The above described embodiment is only one possible configuration of the present invention. Other configurations will also become apparent to one of skill in the art in view of the present disclosure. Suture spacer 60 may be constructed in any of a variety of way which will be well understood by one of skill in the art of constructing medical devices, such as by injection molding. Suture spacer 60 is constructed from a group of materials including thermoplastic elastomers, polyethylene, polypropylene, ABS, polycarbonate nylon, rubber material, other plastics and stainless steel.

EXAMPLE 2

The use of the suture spacer in a transvaginal bladder neck stabilization procedure will now be described. A sling is introduced into a pocket between the urethra and the upper vaginal wall as described in Example 1. As shown in FIG. 8, the suture spacer 60 is placed on suture 45 such that the surface contacting sides 68 and 78 contact the sling 130. As discussed above, first member 62 and second member 72 may be moved relative to one another to facilitate introduction of a suture 45 into the suture receiving site 84. Alternatively, the suture may be introduced past flexible protuberances 88 and 90.

Once a suture 45 has been introduced into the suture receiving site 84, the movement of the suture spacer 60 is limited to sliding on the suture itself. Movement of suture spacer 60 may be further limited by looping the ends of the suture about each other over the device. Limiting the movement of the suture spacer 60 in the surgical field eliminates the need of additional assistance, which could obscure the surgical field. With suture 45 introduced, the ends of the suture 45 may be drawn together and formed into a suture knot on the knot formation sides on 70 or 80 of the first member 62 or the second member 72.

Once the knot is tied, the superfluous suture is severed and the suture spacer 60 is removed, creating suture slack. Following removal of the suture spacer, the treatment is identical to the procedure following suture spacer removal described in Example 1 above.

In another embodiment, the suture spacer comprises a body having a surface contacting end for contacting a surface from which one or more sutures emanate and a knot formation end at which a suture knot is formed. The knot formation end is located on the opposite end of the body from the surface contacting end. The body of this suture spacer also has a suture receiving lumen extending therethrough and a longitudinal axis running parallel to the suture receiving lumen. The body of this embodiment further comprises a slot extending parallel to the longitudinal axis. The slot is in fluid communication with the suture receiving lumen. The preselected amount of slack created by this embodiment is determined by the distance from a surface from which one or more sutures emanate to the knot formation end of the body and back again.

The above described suture spacer embodiment of the present invention is shown in FIGS. 9 through 14. FIG. 10 shows a top view of suture spacer 100. This embodiment includes a body 102. There is also shown a surface contacting end 104, a suture receiving lumen 108, and a suture receiving slot 110. The embodiment shown in FIG. 10 also includes a forceps tang 112 which can be used to hold or manipulate the suture spacer. However, in other embodiments of the suture spacer, the forceps tang may be absent. FIG. 10 also shows suture spacer 100 with a tang handle 114. The tang handle may also be absent from the present invention.

Suture spacer 100 also has a knot formation end 106, adjacent to which a suture knot is tied. FIG. 9 and FIG. 11 show the relationship of the surface contacting end 104 to the knot formation end 106.

The body may have any of a variety of cross-sectional configurations. For example, the body may be cylindrical, rectangular or hexagonal in cross-section.

Figure 13:
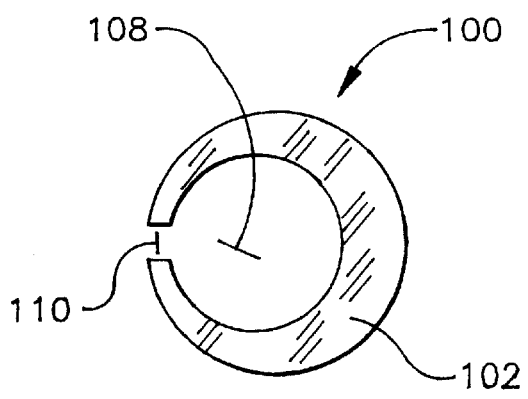
FIG. 13 is a top view of the embodiment shown in FIG. 12.

The body 102 may be substantially rigid or substantially flexible. In an alternative preferred embodiment, some portions of the body may be both substantially rigid while other portions of the body are substantially flexible. In a preferred embodiment, a substantially rigid body is used. FIG. 13 shows a cross-section of a substantially rigid embodiment of suture spacer 100, where the walls of the body on either side of the slot 110 are substantially rigid.

In a substantially flexible embodiment, a predetermined amount of suture slack may be created by the surgeon by tensioning the suture upon the knot formation end 106 so that the distance between the knot formation end 106 and the surface contacting end 104 is reduced. Preferably, a substantially flexible embodiment would be constructed of a suitable material which would cease to compress when a predetermined distance between the knot formation end 106 and the surface contacting end 104 was achieved.

Alternatively, a surgeon using a substantially flexible embodiment could tension a suture, thereby compressing the suture spacer, to a point where other indicia, such as fascial tissue displacement, indicated an appropriate amount of suture slack. Tension off the suture/sling should be minimal. With the patient in the dorsal lithotomy position, the tension should be acceptable when the bladder neck is snugged but not elevated. This will create a "floor" against downward mobility during micturition.

Figure 14:
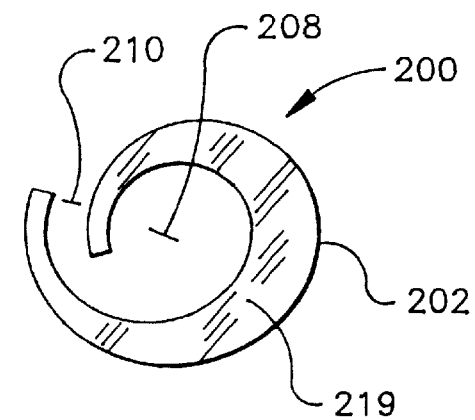
FIG. 14 is a top view of another embodiment of the suture spacer of the present invention.

FIG. 14 illustrates cross-section of a flexible suture spacer 200 embodiment of the present invention. In this embodiment, the walls of the body 202 are flexible permitting introduction of a suture through the suture receiving slot 210 and past flexible walls of the body 202. In suture spacer 200, a rigid backbone may be provided when the suture retaining lumen is set off-center in the cylinder.

In this embodiment, a body portion 219 results from the off-center placement of the suture receiving lumen 208 from the axis of symmetry of the body 202. The body portion 219 results from a differential distribution of body material such that different portions of the suture spacer 200 have different thicknesses. A rigid backbone may be introduced into the body portion 219. The optional rigid backbone may be used to provide a base for a forceps tang.

In an alternative embodiment, the material of the body 202 may have flexible portions adjacent to the suture receiving slot 210 but a rigid structure adjacent to body portion 219. In still another embodiment suture spacer 200 may be composed of a flexible, compressible material and may lack a rigid backbone altogether.

In FIG. 13 a top view of suture spacer 100 is shown where the suture receiving lumen 108 is disposed within the body 102 and functions to releasably retain a suture. Suture receiving lumen 108 may be centered within the body 102 or it may be located off-center within the body. In FIG. 13, suture spacer 100 is shown illustrating the off-center placement of suture receiving lumen 108. Such a placement creates a differential distribution of body 102 material such that different portions of the suture spacer 100 have different thicknesses. This differential in thickness may be used to house other elements of the invention such as a rigid backbone as discussed above.

Suture spacer 100 also consists of suture receiving slot 110 which is of sufficient width to permit suture introduction into suture receiving lumen 108.

As seen in FIG. 11, a forceps tang 112 may be added to the present embodiment. Forceps tang 112 may also comprise gripping ridges 116 to facilitate manipulation during use. A tang handle 114 is also shown. In some embodiments, the tang handle 114 may be omitted as seen in the embodiment shown in FIG. 12.

In one embodiment, the suture receiving lumen 108 has a diameter of about 0.001 to 1 inch wide. In another embodiment, the suture receiving lumen 108 has a diameter of about 0.05 to 0.5 inches wide. In a highly preferred embodiment, the suture receiving lumen 108 of suture spacer 100 has a diameter of about 0.1 inches. In this highly preferred embodiment, the diameter of body 102 is about 0.150 inches. This highly preferred embodiment also has a forceps tang 112 shown in FIG. 11.

In one embodiment, the suture receiving slot 110 may vary in size from about 0.001 to 0.05 inches wide. In another embodiment, the suture receiving slot 110 may vary in size from about 0.005 to 0.025 inches wide. In the highly preferred embodiment shown in FIG. 10, the suture receiving slot 110 is about 0.01 inches wide.

The above described embodiment is only one possible configuration of the present invention. Other configurations will also become apparent to one of skill in the art in view of the present disclosure. Suture spacer 100 may be constructed in any of a variety of ways which will be well understood by one of skill in the art of constructing medical devices, such as by injection molding. A highly preferred embodiment of suture spacer 100 is constructed from acrylonitrile butadiene styrene resin (ABS), but other materials contemplated include but are not limited to thermoplastic elastomers, polyethylene, polypropylene, polycarbonate, nylon, rubber material, other plastics and stainless steel.

EXAMPLE 3

Figure 12:
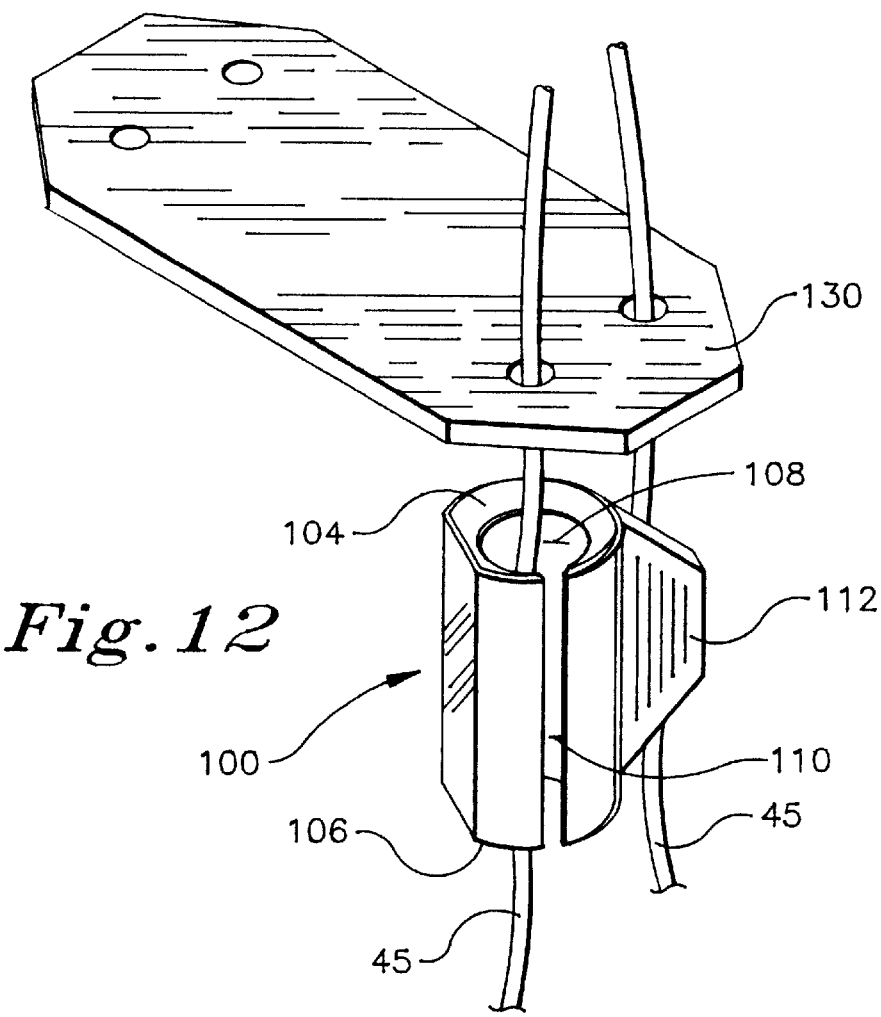
FIG. 12 is a perspective view of another embodiment of the suture spacer depicted in FIG. 9 with a length of suture running through its central lumen and through suture receiving sites in a sling used for improving urinary incontinence.

A sling is inserted between the urethra and the upper vaginal wall as described in Example 1 above. When the suture spacer 100 is used in a surgical procedure, it operates to provide a reproducible amount of suture slack when used to tie a suture knot. In such a procedure, the suture spacer 100 positioned with the surface contacting end 104 in contact with a surface from which one or more sutures emanate. As shown in FIG. 12, suture 45 is introduced through the suture receiving slot 110 and into the suture receiving lumen 108. Next, the sutures 45 are drawn together, forcing the suture spacer 100 against sling 130. The suture spacer is retained in position on the suture after the sutures are drawn together allowing the physician to use both hands to tie a knot in the suture.

Once a suture 45 has been introduced into the suture receiving lumen 108, the movement of the suture spacer 100 is limited to sliding on the suture itself. Movement of suture spacer 100 may be further limited by looping the ends of the suture about each other over the device. Limiting the movement of the suture spacer 100 in the surgical field eliminates the need of additional assistance, which could obscure the surgical field. With suture 45 introduced, the ends of the suture may be drawn together and formed into a suture knot.

A suture knot is preferably tied at the knot formation end 106. The amount of slack produced by suture spacer 100 is determined by the distance between the surface contacting end 104 and the knot formation end 106 and back again. Once the knot is tied, the superfluous suture is severed and the suture spacer 100 is removed, creating suture slack.

A method for using suture spacer 118 which contains no rigid backbone entails the following steps. As described above, suture spacer 118 is positioned with the surface contacting end 104 in communication with a sling. A suture is then introduced through the suture receiving slot 110 and into the suture receiving lumen 108. Next, the sutures are drawn together and a suture knot is formed at the knot formation end 106. However, unlike the rigid embodiments discussed above, the flexible suture spacer 118 compresses in response to the drawing of the sutures to form the suture knot.

The amount of slack produced by suture spacer 118 is determined by the distance between the surface contacting end 104 and the knot formation end 106 and back again when the spacer is maximally compressed. Once the knot is tied, the superfluous suture is severed and the suture spacer 100 is removed, creating suture slack. The suture spacer may also be used above the sling.

Following removal of the suture spacer 100, the treatment of the patient is identical to the procedure following suture spacer removal described in Example 1 above.

In still another embodiment, the suture spacer comprises an elongate body having a surface contacting side for contacting a surface from which one or more sutures emanate and a knot formation side adjacent to which a suture knot is formed. This embodiment further comprises one or more suture receiving sites extending between the surface contacting side and knot formation side and positioned so as to facilitate the removal of the device upon completion of the surgical procedure in which it is used. This embodiment also has a first and second side which are perpendicular to the knot formation side and the surface contacting side. The distance between the first and second sides defines the longitudinal axis. The preselected amount of slack created by this embodiment is measured by the distance from the surface contacting side to the knot formation side and back again.

The above described embodiment is shown in FIGS. 15 and 16. FIG. 15 is a perspective view of the suture spacer 120 which includes an elongate body 122, a surface contacting side 124, a knot formation side 126 and one or more suture receiving sites 128 positioned to facilitate the removal of the suture spacer 120. The elongate body 122 should be substantially flexible.

The ovoid shape of the elongate body 122 of suture spacer 120 shown in FIG. 15 is only one possible embodiment of the present invention. The suture spacer 120 could be substantially spherical, rectangular, substantially triangular, or may have any of a variety of configurations compatible with its intended use.

In the present embodiment, suture slack is determined as a function of the height of suture spacer 120. The height of elongate body 122 of suture spacer 120 is defined as the distance between the surface contacting side 124 and the knot formation side 126.

The height of the suture spacer 120 is largely determinative of the quantity of suture slack generated when this embodiment is used in a surgical procedure. If the elongate body 122 is substantially flexible, it is the final height of the suture spacer 120 after compression plus the distance from the surface from which sutures emanate to the knot formation side that will determine the amount of suture slack created.

In a substantially flexible embodiment of suture spacer 120, a predetermined amount of suture slack may be created by the surgeon by tensioning the suture adjacent to the knot formation side 126 so that the distance between the knot formation side 126 and the surface contacting side 124 is reduced. Preferably, a substantially flexible embodiment would be constructed of a suitable material which would cease to compress when a predetermined distance between the knot formation side 126 and the surface contacting side 124 was achieved. Alternatively, a surgeon using a substantially flexible embodiment could tension a suture, thereby compressing the suture spacer, to a point where other indicia, such as fascial tissue displacement, indicated an appropriate amount of suture slack.

Suture spacer 120 further consists of one or more suture receiving sites 128 to releasably retain sutures during use. The suture receiving sites are positioned in locations which facilitate removal of the suture spacer upon completion of the surgical procedure. In a preferred embodiment, the suture receiving sites 128 are positioned such that suture is generally perpendicular to the longitudinal axis of symmetry of the elongate body after it is introduced into the suture receiving site. The longitudinal axis of symmetry of the elongate body 122 is defined by a first side 127 and a second side 129 on the elongate body 122.

The embodiment illustrated in the FIGS. 15 and 16 shows the suture receiving sites 128 facing in the same direction. However, in another preferred embodiment of suture spacer 120 the suture receiving sites 128 are facing in opposite directions, yet still perpendicular to the longitudinal axis of symmetry.

The embodiment illustrated in the FIGS. 15 and 16 has two suture receiving sites depicted. However, a suture spacer 120 with only one suture receiving sites is contemplated.

The present invention contemplates the use of one suture spacer 120 to create the desired amount of suture slack. Preferably, in such an embodiment, two suture receiving sites 128 are present and both sites would simultaneously contain suture during the knot tying procedure.

Alternatively, in a suture spacer 120 with only one suture receiving site 128, one suture spacer 120 could be used per pair of sutures to be tied into a knot. In such a case, the suture spacer 120 would first be used on one set of sutures to tie a suture knot, and then suture spacer 120 would be moved to the next set of sutures to tie the next knot. This process would continue until all sutures were knotted. However, it is preferred that a plurality of suture spacers be used in a surgical procedure.

The dimensions of the suture spacer 120 will vary according to the desired amount of predetermined suture slack to be generated. In one embodiment, the suture spacer 120 has a height from about 0.1 to 2.0 inches. In another embodiment, the suture spacer 120 has a height from about 0.20 to 0.80 inches. In a highly preferred embodiment, the suture spacer 120 has a height from about 0.6 inches.

Suture spacer 120 may be constructed in any of a variety of ways familiar to those of skill in the art of constructing medical devices. Suture spacer 120 may be constructed from a variety of materials including thermoplastic elastomers, PET, PETG, rubber material, or more rigid materials if ribbed or bendable CABS, polycarbonate, nylon, polypropylene, polyethylene.

The use of suture spacer 120 in a transvaginal procedure to create a preselected amount of suture slack is discussed below in Example 4.

EXAMPLE 4

A sling is positioned between the urethra and the upper vaginal wall as described in Example 1. Referring to FIG.

16, when the suture spacer 120 is used in a surgical procedure, it operates to provide a reproducible amount of suture slack when used to tie a suture knot. The suture spacer 120 is positioned with the suture receiving sites 128 above the sling 130. The surface contacting side 124 is positioned in contact with the upper portion of the pocket so that suture 45 can be introduced into suture receiving sites 128. The sutures 45 are then inserted into the suture receiving sites of the device. Next, the sutures 45 are drawn together and formed into a suture knot 134 on the sling 130.

FIG. 16 shows the relationship of the suture spacer 120, the upper portion of the pocket 135, the sling 130, the urethra 132 and the sutures 45 after a suture knot 134 has been tied. In this FIG., the suture spacer 120 is positioned under the urethra 132 in the tissue between the urethra and the upper vaginal wall. Once the suture knots 134 are tied, the superfluous suture is severed and the suture spacer 120 is removed, creating suture slack. The suture spacer 120 is removed laterally if the suture receiving sites 128 are located on the same side of the suture spacer. If the suture receiving sites are located on opposite sides of the suture spacer 120, the spacer is first rotated to remove the sutures 45 from the suture receiving sites 128 and then the spacer is removed. The amount of slack produced by suture spacer 120 is determined by the distance between the surface contacting side 124 and the knot formation side 126. Following removal of the suture spacer, treatment of the patient is identical to the procedure following suture spacer removal described in Example 1 above.

In another embodiment, the suture spacer comprises a body having a surface contacting side for contacting a surface from which one or more sutures emanate and a knot formation side adjacent to which a suture knot is tied. The surface contacting side and the knot formation side also have outer surfaces. This embodiment also has an engagement member comprising an engagement body and at least one securing portion that is movable from a first position in which the at least one securing portion and the surface contacting side engage the surface from which one or more sutures emanate to a second position in which the at least one securing portion releases the surface from which one or more sutures emanate. The desired amount of slack created by this embodiment is measured by the distance from a surface contacting side to the knot formation side and back again.

FIGS. 17 through 21 show suture spacer 140 of the present invention. Referring to FIG. 18, there is shown a front view of the suture spacer 140 which includes a body 142, having a surface contacting side 144 and a knot formation side 146. The suture spacer 140 also includes an engagement member 148 comprising an engagement body 150 and at least one securing portion 152.

As shown in FIG. 18, a surface contacting side 144 facilitates contact of suture spacer 140 with a surface from which sutures emanate. The surface contacting side 144 has outer surfaces 149.

In some embodiments, the suture spacer 140 may further comprise a knot formation side 146 adjacent to which a suture knot is tied. In some embodiments, the knot formation side 146 of the body 142 may have a knot formation site 153 upon which a suture knot may be tied. Alternatively, in some embodiments a knot formation site 153 may be on a portion of the engagement member 148 which extends along the knot formation side 146 of the body 142. The knot formation side 146 has outer surfaces 151.

FIG. 20 shows a side view of suture spacer 140 and more clearly illustrates knot formation side 146. Preferably the knot formation site 153 is in the center of the portion of the engagement member 148 on the knot formation side 146 of the body 142 or the center of the knot formation side 146 of the body 142.

The engagement member 148 of suture spacer 140 facilitates the reversible securing of the suture spacer 140 to a suture emanating surface such as a sling 171. The engagement member 148 may be substantially rigid. The engagement member may be disposed within the body 142 or it may reside upon the outer surfaces 149 and/or 151 of the body 142. The engagement member 148 further consists of an engagement body 150 and at least one securing portion 152. In some embodiment, the engagement body 150 contacts the body 142 of suture spacer 140. The engagement member 148 may also include pressure points 159.

The engagement member 148 may protrude directly from the body 142, or it may protrude from any other portion of the suture spacer 140, or it may extend along the outer surfaces 149 of the contacting member 145 and the knot formation side 146. In some embodiments the engagement member 148 has a suture groove 156 running along it for releasably retaining a suture. Preferably, suture groove 156, shown in FIG. 19, is also present on securing portion 152. Suture groove 156 partially encompasses a suture when the engagement member 148 and the securing portion 152 are engaged on a sling or other surface from which sutures emanate.

The securing portion 152 operates to hold the suture spacer 140 in contact with a suture emanating surface such as a sling 171. There may be one or more engagement members included in suture spacer 140. The embodiment in FIG. 18 shows one such engagement member 148 having two securing portions 152 thereon. The body of the engagement member 148 may extend through the knot formation side 146 or along the exterior of the knot formation side 146. FIG. 19 is a cross-sectional view of the suture spacer 140 illustrating the securing portion 152 in contact with a suture emanating surface such as a sling 171.

The securing portion 152 should be of sufficient length to releasably hold the suture spacer 140 securely to the surface from suture emanating surface such as a sling 171. The pressure point 159 may be disposed on the engagement member 148 to move the securing portion 152 between a first position and second position. The first position, in which the securing portion 152 and the surface contacting side of the body 142 are generally parallel, facilitates engagement of a surface from which one or more sutures emanate. The second position, the securing portion 152 is in a retracted and generally perpendicular to the surface contacting side 144 and the surface from which one or more sutures emanate. The retracted orientation of the securing portion 152 in the second position facilitates the engagement and disengagement of the suture spacer 140 from a sling or suture emanating surface such as a sling 171.

Figure 21:
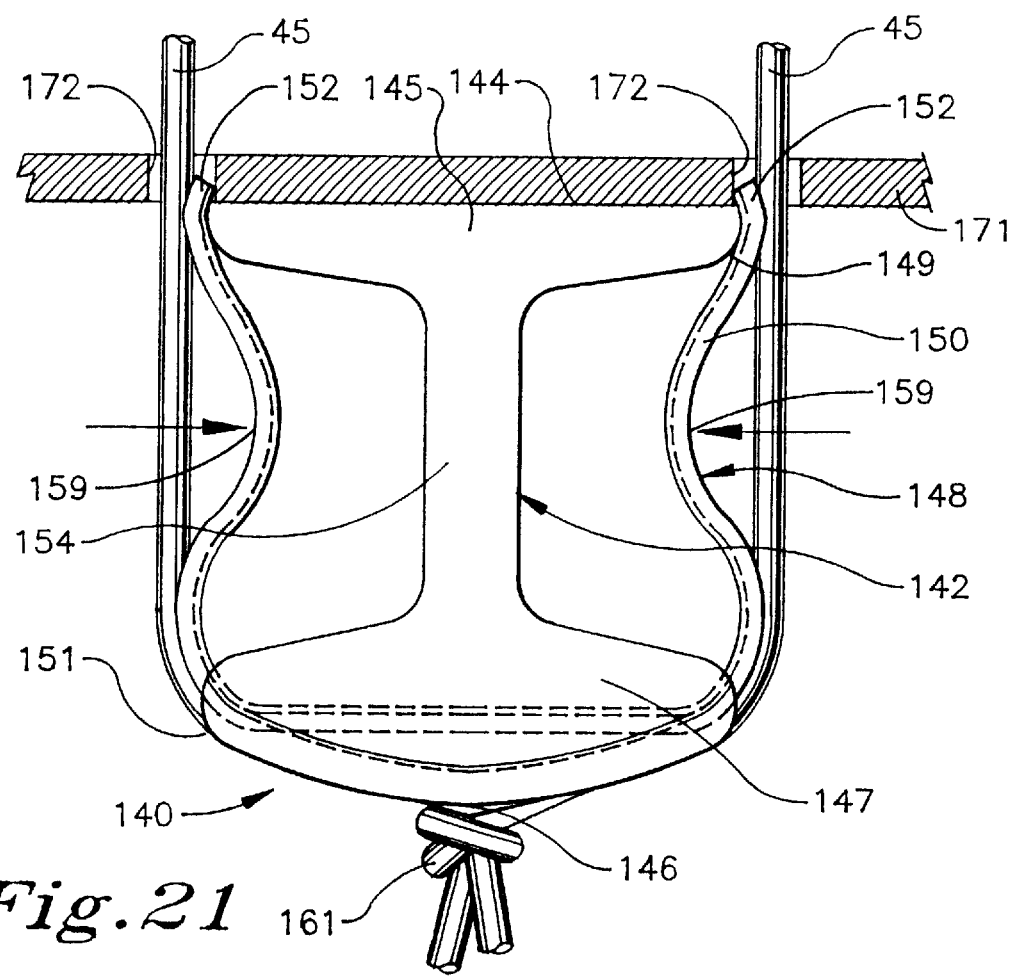
FIG. 21 is a front view of the embodiment shown in FIG. 17 in a preattached position.

To illustrate, application of pressure to the pressure points 159 causes the securing portions 152 to move from the first position depicted in FIG. 18 in which they are positioned above and generally parallel to the surface contacting side to the second position shown in FIG. 21 in which the securing portions are retracted and not parallel to the surface contacting side.

As illustrated in FIG. 18, in some embodiments the suture spacer 140 may also comprise a connector 154 disposed between the surface contacting side 144 and the knot formation side 146. Connector 154 creates distance between the surface contacting side 144 and the knot formation side 146. This distance is a factor in measuring a predetermined amount of suture slack when using suture spacer 140. Alternatively the surface contacting site 144 and the knot formation side 146 may be on opposite sides of a unitary body.

The present embodiment is generally arch-shaped. However, other shapes of the suture spacer would be generally apparent to one of skill in the art. Examples include but are not limited to, a generally triangular shaped suture spacer and a generally rectangular shaped suture spacer. Accordingly, suture spacer 140 may be constructed in any of a variety of ways which will be well understood by one of skill in the art of constructing medical devices. Furthermore, materials suitable for construction of the substantially flexible or substantially rigid components of suture spacer 140 which are known to one skilled in the art for use in surgical devices may be used. The body 142 of suture spacer 140 may be constructed from a variety of materials including but not limited to rigid thermoplastic elastomers, nylon, polycarbonate, ABS, polypropylene, polyethylene, other plastics and stainless steel. The engagement body 150 of suture spacer 140 may in turn be constructed from a variety of materials including but not limited to polycarbonates, ABS, nylon, rubber material, other plastics and stainless steel. However, any suitable material known to one of skill in the art of constructing surgical devices may be used.

EXAMPLE 5

The use of the suture spacer in a transvaginal bladder neck stabilization procedure using the embodiment shown in FIGS. 17–21 will now be described. A sling is introduced into a pocket between the urethra and the upper vaginal wall as described in Example 1. In one embodiment, sutures are already threaded through apertures 172 of the sling. In an alternative embodiment, one suture is passed through the sling apertures around the engagement member 146 again through the sling apertures 172 from above. In yet another alternative, the sutures are not pre-threaded through the sling 172. Pressure is placed on pressure points 159 located on the sides of the engagement member 148 which moves the securing portions 152 from a first position in which the securing portions 152 are above and generally parallel to the surface contacting side 144 to a second position (shown in FIG. 21) in which the securing portions 152 are retracted to facilitate attaching the suture spacer 140 to a sling. Attachment is facilitated by aligning the securing portions 152 to penetrate the sling apertures 172. The securing portion 152 of the engagement member 148 is then inserted into the sling aperture 172. After insertion, pressure is released from the pressure points 159, moving the securing portions 152 from a second position to a first position in which the securing portions 152 engage the sling 171. FIG. 17 illustrates the use of two suture spacers 140 on a sling 171 under a urethra 132. In this figure the securing portions 152 are shown protruding through the sling apertures 172 and holding suture spacer 140 in communication with a sling 171. FIG. 17 also shows that once the securing portions 152 have secured suture spacer 140 to the sling, the suture spacer 140 may be used in a hands-free fashion since the suture spacer 140 is attached to the suture emanating surface such as a sling 171.

With suture spacer 140 in position, the sutures are partially seated in suture groove 156 and extend past the knot formation side 146. The ends of the suture are drawn together and formed into a suture knot 161 adjacent to the knot formation side 146. Once the suture knot 161 is tied and superfluous suture is removed, pressure is again applied to the pressure points 159. This applied pressure realigns the securing portions 152 of the engagement members 150 with respect to the sling, from the engaged first position in which the securing portions are aligned generally parallel to the sling and the surface contacting side 144 to a disengaged second position where the securing portions 152 are retracted to facilitate removal of suture spacer 140, as shown in FIG. 21.

The suture spacer 140 is then removed from the sling, leaving suture slack. The predetermined amount of suture slack generated is dependent on the shape of the suture spacer used in the procedure. The distance from the surface from which one or more sutures emanate to the knot formation side 146 and back again determines the predetermined amount of suture slack which is introduced into the suture. After removal of the suture spacer 140 the patient is treated as described in Example 1 above.

Another embodiment of the present invention is a suture spacer comprising a shaft having a proximal end and a distal end, a connector connected to the shaft, and a slack defining member connected to the spacer. The slack defining member has a surface contacting side for contacting a surface from which one or more sutures emanate and a knot formation side adjacent to which a suture knot is formed. The knot formation side is disposed opposite to the surface contacting side. A preselected amount of suture slack created with this embodiment is determined by the distance from a surface from which sutures emanate to the knot formation side of the slack defining member and back again.

Figure 22:
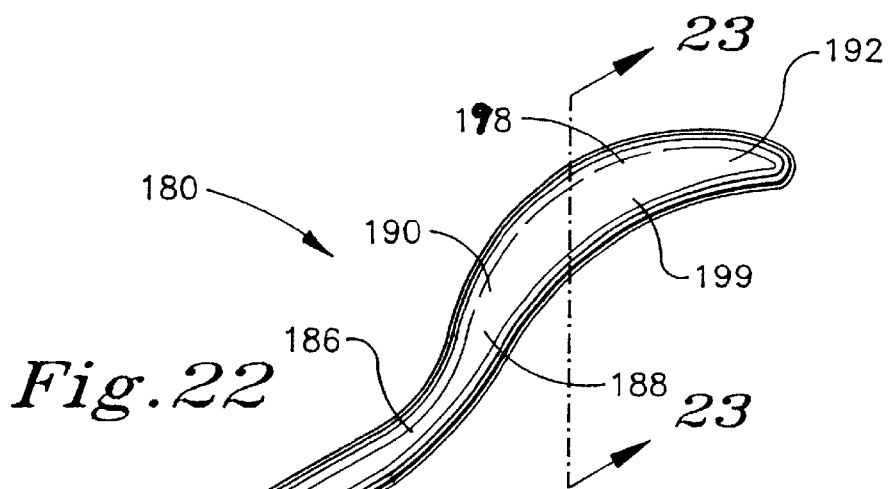
FIG. 22 is a perspective view of another embodiment of the present invention.

FIG. 22 is a perspective view of this embodiment. Suture spacer 180 has a shaft 182 comprising a proximal end 184 and a distal end 186. The suture spacer 180 has a connector 188 which is attached to the distal end 186 of the shaft 182. The suture spacer 180 also has a slack defining member 192 which is in turn attached to the connector 188 at connecting side 190. The slack defining member 192 further comprises a surface contacting side 198 and a knot formation side 199. The connector 188 may be attached to the shaft 182 at an angle in order to properly orient the slack defining member 192 with respect to the shaft 182. The angle of connection should be one which facilitates the use of suture spacer 180 transvaginally. Both the slack defining member 192 and the shaft 182 have longitudinal axis of symmetry. Preferably, the longitudinal axes of both the shaft 182 and slack defining member 192 are parallel.

Figure 23:
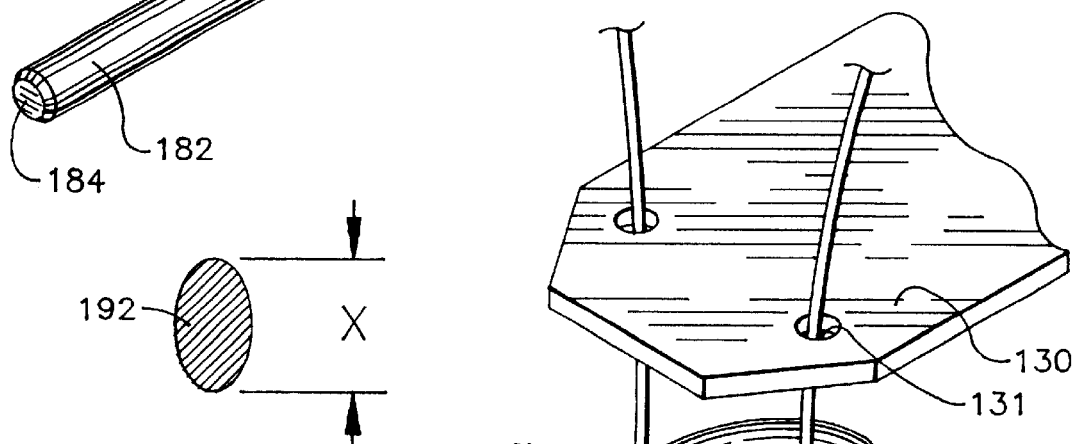
FIG. 23 is a cross-sectional view of the embodiment in FIG. 22 taken along line 23—23.

The amount of slack generated using suture spacer 180 is determined by the size and shape of the slack defining member 192. To illustrate, a cross-section of the slack defining member from FIG. 22 is shown in FIG. 23. The amount of slack generated will be a function of the height and shape of the slack defining member 192. The height of the slack defining member 192 is defined as the distance between the surface contacting side 198 and the knot formation side 199. The height of a highly preferred embodiment of suture spacer 180 is shown as distance X in FIG. 23. The final amount of slack generated using suture spacer 180 will be equal to the distance from the suture emanating surface to the knot formation site, and then back again.

The above described embodiment is only one possible configuration of the present invention. Other configurations will also become apparent to one of skill in the art in view of the present disclosure. For example, the slack defining member 192 may have any of a variety of cross-sectional shapes compatible with the intended use of the suture spacer, including spherical, rectangular, triangular, and ovoid. Suture spacer 180 may be constructed in any of a variety of ways which will be well understood by one of skill in the art of constructing medical devices, such as by injection molding. Suture spacer 180 may be constructed from a variety of materials including rigid thermoplastic elastomers, polycarbonates, ABS, nylon, polypropylene, polyethylene, rubber material, other plastics and stainless steel.

Example 6 describes the use of suture spacer 180 in a transvaginal bladder neck stabilization procedure. When the suture spacer 180 is used in a transvaginal surgical procedure, it operates to provide a reproducible amount of suture slack when a suture knot is tied.

EXAMPLE 6

Figure 24:
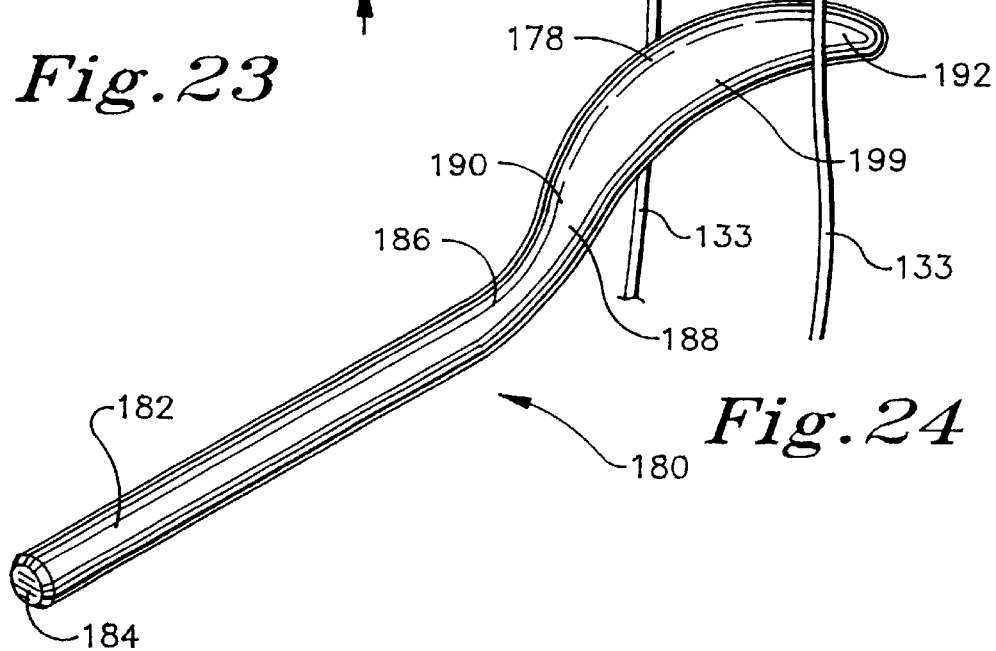
FIG. 24 is a perspective view of the embodiment depicted in FIG. 22 positioned beneath a sling.

A sling is positioned between the urethra and the upper vaginal wall as described in Example 1. FIG. 24 shows a perspective view of suture spacer 180. Two sutures 133 are seen protruding through the sling apertures 131 of sling 130. The suture spacer 180 is inserted between the two apertures 131. The sutures 133 are then drawn over the knot formation side 199 of the slack defining member 192 and knotted. The loose ends of the suture are then cut, leaving knotted suture. Once suture spacer 180 is removed from the suture, slack is created. After removal of the suture spacer, the patient is treated as described in Example 1 above.

The suture spacer 180 may also be used above the sling to create a predetermined amount of suture slack. The procedure is essentially the same as where as when the spacer is used below with suture spacer resting on the tissue dissection.

Although this invention has been described in terms of certain preferred embodiments, other embodiments which will be apparent to those of ordinary skill in the art in view of the disclosure herein are also with the scope of this invention. Accordingly, the scope of the invention is intended to be defined only by reference to the appended claims. All documents cited herein are incorporated herein by reference in their entirety.

What is claimed is:

1. A method of spacing a suture in a surgical procedure, the method comprising the steps of:
   a. providing a suture spacer comprising:
      (i) a first member including a proximal end and a distal end;
      (ii) a second member including a proximal end and a distal end, a distal portion of the second member comprising a cross-sectional area, the first and second members having a thickness dimension; and
      (iii) a pivot disposed between the first and second members such that the application of a compressive force upon the proximal ends of the first and second members results in movement of the distal ends away from each other;
   b. placing a suture between the first and second members;
   c. tying the suture around the spacer so as to traverse the thickness dimension and the cross-sectional area, the thickness dimension and the cross-sectional area cooperating to create a predetermined amount of slack in the suture; and
   d. compressing the proximal ends and removing the suture from between the first and second members, the suture retaining the predetermined amount of slack.

2. The method of claim 1, wherein:
   the first member further comprises two opposing substantially parallel sides, the sides being separated by the thickness dimension, the distal portion of the first member having a first width substantially perpendicular to the thickness dimension;
   the second member further comprises two opposing substantially parallel sides, the sides being separated by the thickness dimension, the distal portion of the second member having a second width substantially perpendicular to the thickness dimension, the second width being greater than the first width of the first member; and
   the cross-sectional area is substantially defined by the thickness dimension and the second width.

3. The method of claim 2, wherein the second member further comprises a substantially planar exterior surface that is substantially perpendicular to the sides of the second member.

4. The method of claim 3, wherein the substantially planar exterior surface further comprises a ridge for retaining the suture.

5. The method of claim 2, wherein the first member, the second member, and the pivot are integrally formed as a single piece of material.

6. The method of claim 2, wherein the suture spacer further comprises a protuberance for limiting movement of the distal ends of the first and second members away from each other.

7. The method of claim 1, wherein
   the proximal end and distal end of the second member of the suture spacer define a longitudinal axis, and the second member further comprises a surface substantially perpendicular to the longitudinal axis, the surface having a length, the length being greater than the thickness dimension, such that the cross-sectional area is substantially defined by the length and the thickness dimension,
   and the suture spacer further comprises a border for retaining the suture when placed between the first and second members.

8. The method of claim 7, wherein the suture spacer further comprises a protuberance for limiting movement of the distal ends of the members away from each other.

* * * * *